United States Patent
Ogura et al.

(10) Patent No.: US 12,014,538 B2
(45) Date of Patent: *Jun. 18, 2024

(54) METHOD, SYSTEM, AND MEDIUM HAVING STORED THEREON INSTRUCTIONS THAT CAUSE A PROCESSOR TO EXECUTE A METHOD FOR OBTAINING IMAGE INFORMATION OF AN ORGANISM COMPRISING A SET OF OPTICAL DATA

(71) Applicant: Sony Group Corporation, Tokyo (JP)

(72) Inventors: Morio Ogura, Kanagawa (JP); Hirofumi Sumi, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,309

(22) Filed: Apr. 7, 2023

(65) Prior Publication Data

US 2023/0245446 A1 Aug. 3, 2023

Related U.S. Application Data

(63) Continuation of application No. 17/713,639, filed on Apr. 5, 2022, now Pat. No. 11,875,562, which is a (Continued)

(30) Foreign Application Priority Data

Mar. 25, 2013 (JP) .................................. 2013-062017

(51) Int. Cl.
*G06V 20/10* (2022.01)
*A01G 7/00* (2006.01)
(Continued)

(52) U.S. Cl.
CPC ............. *G06V 20/188* (2022.01); *A01G 7/00* (2013.01); *G01J 3/36* (2013.01); *G01J 3/513* (2013.01);
(Continued)

(58) Field of Classification Search
CPC ........ A01G 7/00; H04N 13/204; H04N 23/11; G01C 11/02; G01J 3/36; G01J 3/51;
(Continued)

(56) References Cited

U.S. PATENT DOCUMENTS

| 4,519,193 A | 5/1985 | Yoshida et al. |
| 6,160,902 A | 12/2000 | Dickson et al. |

(Continued)

FOREIGN PATENT DOCUMENTS

| CN | 101839979 A | 9/2010 |
| CN | 102013021 A | 4/2011 |

(Continued)

OTHER PUBLICATIONS

International Search Report and Written Opinion dated Jun. 26, 2014 in connection with International Application No. PCT/JP2014/001497.

(Continued)

*Primary Examiner* — Katrina R Fujita
(74) *Attorney, Agent, or Firm* — Wolf, Greenfield & Sacks, P.C.

(57) ABSTRACT

The present disclosure relates to methods and systems for obtaining image information of an organism including a set of optical data; calculating a growth index based on the set of optical data; and calculating an anticipated harvest time based on the growth index, where the image information includes at least one of: (a) visible image data obtained from an image sensor and non-visible image data obtained from the image sensor, and (b) a set of image data from at least two image capture devices, where the at least two image capture devices capture the set of image data from at least two positions.

15 Claims, 19 Drawing Sheets

Related U.S. Application Data continuation of application No. 16/812,678, filed on Mar. 9, 2020, now Pat. No. 11,699,286, which is a continuation of application No. 14/777,549, filed as application No. PCT/JP2014/001497 on Mar. 17, 2014, now Pat. No. 10,607,078.

(51) Int. Cl.

| | | |
|---|---|---|
| G01J 3/28 | (2006.01) | |
| G01J 3/36 | (2006.01) | |
| G01J 3/51 | (2006.01) | |
| G01N 21/01 | (2006.01) | |
| G01N 21/17 | (2006.01) | |
| G01N 21/25 | (2006.01) | |
| G01N 21/31 | (2006.01) | |
| G01N 21/359 | (2014.01) | |
| G01N 21/84 | (2006.01) | |
| G01N 33/00 | (2006.01) | |
| G06Q 30/00 | (2023.01) | |
| G06Q 50/02 | (2024.01) | |
| G06T 7/00 | (2017.01) | |
| H04N 13/204 | (2018.01) | |
| H04N 23/11 | (2023.01) | |

(52) U.S. Cl.
CPC ......... *G01N 21/251* (2013.01); *G01N 21/255* (2013.01); *G01N 21/314* (2013.01); *G06Q 30/00* (2013.01); *G06Q 50/02* (2013.01); *G06T 7/0004* (2013.01); *H04N 13/204* (2018.05); *H04N 23/11* (2023.01); *G01J 2003/2826* (2013.01); *G01N 2021/0118* (2013.01); *G01N 2021/1797* (2013.01); *G01N 2021/3155* (2013.01); *G01N 21/359* (2013.01); *G01N 2021/8466* (2013.01); *G01N 33/0098* (2013.01); *G06T 2207/30128* (2013.01); *G06T 2207/30188* (2013.01)

(58) Field of Classification Search
CPC .. G01J 3/513; G01J 2003/2826; G01N 21/25; G01N 21/251; G01N 21/255; G01N 21/314; G01N 21/359; G01N 33/0098; G01N 2021/0118; G01N 2021/1797; G01N 2021/3155; G01N 2021/8466; G06Q 30/00; G06Q 50/02; G06T 7/0004; G06T 2207/30128; G06T 2207/30188; G06V 20/188
See application file for complete search history.

(56) References Cited

U.S. PATENT DOCUMENTS

| | | |
|---|---|---|
| 7,928,352 B2 | 4/2011 | Toda |
| 9,113,590 B2 | 8/2015 | Johnson |
| 10,607,078 B2 | 3/2020 | Ogura et al. |
| 11,443,509 B2 | 9/2022 | Ogura et al. |
| 11,699,286 B2 | 7/2023 | Ogura et al. |
| 2002/0101895 A1 | 8/2002 | Augusto |
| 2004/0264761 A1 | 12/2004 | Mas et al. |
| 2006/0167926 A1 | 7/2006 | Verhey et al. |
| 2006/0213167 A1 | 9/2006 | Koselka et al. |
| 2007/0003107 A1 | 1/2007 | Wei et al. |
| 2007/0005208 A1 | 1/2007 | Han et al. |
| 2008/0087800 A1 | 4/2008 | Toda |
| 2008/0123097 A1 | 5/2008 | Muhammed et al. |
| 2009/0168181 A1 | 7/2009 | Su et al. |
| 2009/0212946 A1 | 8/2009 | Pikaz |
| 2010/0098342 A1 | 4/2010 | Davis et al. |
| 2010/0115830 A1 | 5/2010 | Dube |
| 2010/0140461 A1 | 6/2010 | Sprigle et al. |
| 2010/0223276 A1 | 9/2010 | Al-Shameri et al. |
| 2010/0231755 A1 | 9/2010 | Sekine |
| 2011/0221895 A1 | 9/2011 | Sharma |
| 2011/0235017 A1 | 9/2011 | Iwasaki |
| 2011/0276336 A1 | 11/2011 | Sweely |
| 2012/0086095 A1 | 4/2012 | Nishiyama et al. |
| 2012/0109614 A1 | 5/2012 | Lindores |
| 2012/0155714 A1 | 6/2012 | Douglass et al. |
| 2012/0237083 A1 | 9/2012 | Lange et al. |
| 2012/0250962 A1 | 10/2012 | Scharf |
| 2013/0141589 A1 | 6/2013 | Lin et al. |
| 2014/0093138 A1 | 4/2014 | Naganuma et al. |
| 2016/0283791 A1 | 9/2016 | Ogura et al. |
| 2020/0210699 A1 | 7/2020 | Ogura et al. |
| 2020/0356775 A1 | 11/2020 | Ogura et al. |
| 2022/0230431 A1 | 7/2022 | Ogura et al. |

FOREIGN PATENT DOCUMENTS

| | | |
|---|---|---|
| CN | 102521564 A | 6/2012 |
| CN | 102565061 A | 7/2012 |
| JP | 2006-250827 A | 9/2006 |
| JP | 2007-310463 A | 11/2007 |
| JP | 2010-166851 A | 8/2010 |
| JP | 2011-027600 A | 2/2011 |
| JP | 2011-203874 A | 10/2011 |
| KR | 20050043368 A | 5/2005 |
| WO | WO 9919824 A1 | 4/1999 |
| WO | WO 2003/069315 A | 8/2003 |
| WO | WO 2009/116613 A1 | 9/2009 |
| WO | WO-2009153983 A1 | 12/2009 |
| WO | WO 2010/063075 A1 | 6/2010 |

OTHER PUBLICATIONS

International Preliminary Report on Patentability dated Oct. 8, 2015 in connection with International Application No. PCT/JP2014/001497.
Article 94(3) Communication dated May 31, 2017 in connection with European Application No. 14719877.4.
Chinese Office Action dated May 31, 2017 in connection with Chinese Application No. 201480016948.4 and English translation thereof.
Korean Office Action dated Jun. 1, 2020 in connection with Korean Application No. 10- 2015-7021071, and English translation thereof.
European Communication pursuant to Article 94(3) EPC dated Dec. 7, 2020 in connection with European Application No. 14719877.4.
Dworak et al., Strategy for the development of a smart N DVI camera system for outdoor plant detection and agricultural embedded systems. Sensors 13.2 (Jan. 2013): 1523-1538.
Garrity et al., A simple filtered photodiode instrument for continuous measurement of narrowband NDVI and PRI over vegetated canopies. Agricultural and Forest Meteorology. Mar. 15, 2010;150(3):489-96.
Hilker et al., Remote sensing of photosynthetic light-use efficiency across two forested biomes: Spatial scaling. Remote Sensing of Environment. Dec. 15, 2010;114(12):2863-74.
Hui et al., Image Segmentation Algorithm for Overlapping Fruits Based on Disparity Map, Agricultural Machinery Journal, Jun. 30, 2012, vol. 43, Issue 6, pp. 167-173.
Leemans et al., A method for plant leaf area measurement by using stereo vision. Proceedings of CIGR-AgEng 2012 International Conference on Agricultural Engineering.
Leuning et al., A multi-angle spectrometer for automatic measurement of plant canopy reflectance spectra. Remote Sensing of Environment. Aug. 15, 2006;103(3):236-45.
Nguy-Robertson et al., Green leaf area index estimation in maize and soybean: Combining vegetation indices to achieve maximal sensitivity. Agronomy Journal. Sep. 2012; 104(5):1336-47.
Rundquist et al., Remote estimation of vegetation fraction in corn canopies. Proceedings of the 3rd European Conference on Precision Agriculture. 2001:301-6.
Sakamoto et al., Assessment of digital camera-derived vegetation indices in quantitative monitoring of seasonal rice growth. ISPRS Journal of Photogrammetry and Remote Sensing 66.6 (2011): 872-882.

(56) References Cited

OTHER PUBLICATIONS

Soudani et al., Ground-based Network of NDVI measurements for tracking temporal dynamics of canopy structure and vegetation phenology in different biomes. Remote sensing of environment. Aug. 1, 2012;123:234-45.
Tanaka et al., An Image Change Detection Application for Field Server. Proc. of IAALD-AFITA-WCCA. 2008:49-54.
Weber et al., Crop Field Reflectance Measurements. AIP Conference Proceedings. American Institute of Physics. Apr. 15, 2008(992)1: 671-76.
Yao et al., Comparison and intercalibration of vegetation indices from different sensors for monitoring above-ground plant nitrogen uptake in winter wheat. Sensors. Mar. 2013;13(3):3109-30.
Andersen et al., Geometric plant properties by relaxed stereo vision using simulated annealing. Computers and electronics in agriculture. Nov. 1, 2005;49(2):219-32.
Rankin et al., Daytime mud detection for unmanned ground vehicle autonomous navigation. Proceedings of the 26th Army Science Conference. Dec. 1, 2008. 10 pages.
Rovira-Más et al., Creation of three-dimensional crop maps based on aerial stereoimages. Biosystems engineering. Mar. 1, 2005;90(3):251-9.
Sun et al., Evaluation of maize growth by ground based multispectral image. 2011 IEEE/SICE International Symposium on System Integration (SII) Dec. 20, 2011:207-11.
Extended European Search Report dated Jun. 29, 2023 in connection with European Application No. 23169780.6.

FIG. 6

| IP ADDRESS | SENSOR POSITION | REGION | TYPE OF AGRICULTURAL PRODUCE | OWNER OF AGRICULTURAL PRODUCE (FARM) | FARM, FIELD Gp | CONTRACT DISTRIBUTOR | CONTRACT RETAILER | GROUP | GROWTH INDEX | ANTICIPATED PROPER HARVEST TIME |
|---|---|---|---|---|---|---|---|---|---|---|
| AAA | A | a | α | KOU | G1 | (1) | AH | ... | 60 | OCTOBER 15TH |
| BBB | B | a | α | KOU | G1 | (1) | AH | ... | 70 | OCTOBER 16TH |
| CCC | C | c | β | OTSU | G2 | (2) | EAH | ... | 65 | OCTOBER 20TH |

METHOD, SYSTEM, AND MEDIUM HAVING STORED THEREON INSTRUCTIONS THAT CAUSE A PROCESSOR TO EXECUTE A METHOD FOR OBTAINING IMAGE INFORMATION OF AN ORGANISM COMPRISING A SET OF OPTICAL DATA

CROSS REFERENCE TO RELATED APPLICATIONS

This application is a continuation of and claims the benefit under 35 U.S.C. § 120 of U.S. patent application Ser. No. 17/713,639, titled "METHOD, SYSTEM, AND MEDIUM HAVING STORED THEREON INSTRUCTIONS THAT CAUSE A PROCESSOR TO EXECUTE A METHOD FOR OBTAINING IMAGE INFORMATION OF AN ORGANISM COMPRISING A SET OF OPTICAL DATA," filed Apr. 5, 2022, which claims the benefit under 35 U.S.C. § 120 of U.S. patent application Ser. No. 16/812,678, titled "METHOD, SYSTEM, AND MEDIUM HAVING STORED THEREON INSTRUCTIONS THAT CAUSE A PROCESSOR TO EXECUTE A METHOD FOR OBTAINING IMAGE INFORMATION OF AN ORGANISM COMPRISING A SET OF OPTICAL DATA," filed Mar. 9, 2020, which claims the benefit under 35 U.S.C. § 120 of U.S. patent application Ser. No. 14/777,549, titled "METHOD, SYSTEM, AND MEDIUM HAVING STORED THEREON INSTRUCTIONS THAT CAUSE A PROCESSOR TO EXECUTE A METHOD FOR OBTAINING IMAGE INFORMATION OF AN ORGANISM COMPRISING A SET OF OPTICAL DATA," filed Sep. 16, 2015, now U.S. Pat. No. 10,607,078, which is a U.S. National Stage Entry of International Application No. PCT/JP2014/001497, filed in the Japanese Patent Office as a Receiving office on Mar. 17, 2014, which claims priority to Japanese Priority Patent Application JP 2013-062017 filed Mar. 25, 2013, each of which is hereby incorporated by reference in its entirety.

TECHNICAL FIELD

The presently disclosed technology relates to an information processing system, an information processing method of the information processing system, an imaging device and an imaging method, and a program, and particularly to an information processing system, an information processing method of the information processing system, an imaging device and an imaging method, and a program that enables calculation of a proper growth index of agricultural produce and an anticipated proper harvest time.

BACKGROUND ART

In satellite remote sensing in which a growth state and a harvest season of agricultural produce are estimated by sensing reflected light (near-infrared light) from plants using a sensor mounted in a space satellite, it is difficult to acquire data under a night sky or clouds, and it takes several days until data from the satellite comes to hand, and thus, real-time information is hard to get. In addition, since a satellite makes a loop trip and thus getting information of a same spot depends on the cycle of the satellite, rough information of a wide range is obtained, while accurate information of a narrow region is difficult to obtain.

In addition, in near remote sensing that uses a sensor installed on the ground, the distance from a target to the sensor is short, and therefore, there are advantages in that sensing is less affected by the atmosphere than in the satellite remote sensing, data from the target alone can be acquired by the sensor without interference between the sensor and the target, data can be acquired at preferable times, and the like. Such a remote sensing technology in which image information is acquired in proximity to a plant, the image information is transmitted to a computer, a vegetation index is computed by the computer, and a proper harvest time is evaluated or anticipated based on the correlation between the index and evaluation items such as an amount of fiber has been disclosed (refer to PTL 1).

CITATION LIST

Patent Literature

PTL 1

International Publication No. WO2009/116613

SUMMARY

Technical Problem

However, in the technology disclosed in PTL 1 described above, since a single camera that photographs agricultural produce is provided, when growth situations of the produce vary within a farm region, the growth situations of the entire farm are recognized with occasionally photographed growth situations of the produce, and thereby there are cases in which accuracy of evaluation or anticipation of a proper harvest time is lowered. Also, prior art technology is limited because it fails to address growth of organisms. In addition, it is not possible to grasp growth situations of many farms located in different regions.

In addition, in the technology disclosed in PTL 1, accuracy in evaluating a growth situation of agricultural produce by computing the vegetation index through an arithmetic operation based on data of near-infrared light and red light from image data of the agricultural produce using a near-infrared light sensor and a red-light sensor is not sufficiently reliable. In other words, it is difficult to improve accuracy of evaluation by performing both evaluation in combination with evaluation of a growth situation using colors of the produce and evaluation of a growth situation based on the vegetation index.

Furthermore, the technology disclosed in PTL 1 discloses that a dedicated device for remote sensing may be used as a camera. For such a dedicated device for remote sensing, a multi-spectral camera (multi-band camera) or a hyper-spectral camera is used. The former necessitates mechanical switching of a band-pass filter, and synchronism of image regions is insufficient. In addition, since the latter necessitates scanning, synchronism of image regions is insufficient, further, since an optical system thereof is complicated, it is difficult to miniaturize the camera which is expensive, and further, since data take a large capacity, a communication load increases, and thus the camera is not appropriate for wireless communication.

Furthermore, the technology disclosed in PTL 1 is based on the premise that the evaluation result or the anticipated proper harvest time should be provided to a producer or a manager. In this case, the producer can anticipate and grasp a harvest time, but it is difficult to satisfy demands of retailers, general consumers, consumers such as restaurants, distributors, or other outside parties who want to purchase agricultural produce without going through a retailer and/or who want to know a harvest time of the produce.

It is desirable to be able to properly compute a growth index and an anticipated proper harvest time of agricultural produce based on an RGB image and an NIR image, and be able to distribute information about the growth index and the anticipated proper harvest time not only to a producer and a manager but also to retailers, general consumers, and distributors, among others.

Solution to Problem

Various embodiments of the present disclosure relate to methods including: obtaining image information of an organism including a set of optical data; calculating a growth index based on the set of optical data; and calculating an anticipated harvest time based on the growth index, where the image information includes at least one of: (a) visible image data obtained from an image sensor and non-visible image data obtained from the image sensor, and (b) a set of image data from at least two image capture devices, where the at least two image capture devices capture the set of image data from at least two positions.

Further embodiments relate to systems including: an image capture device, where at least one of the server and the image capture device is configured to: obtain image information of an organism including a set of optical data; calculate a growth index based on the set of optical data; and calculate an anticipated harvest time based on the growth index, where the image information includes at least one of: (a) visible image data obtained from an image sensor and non-visible image data obtained from the image sensor, and (b) a set of image data from at least two image capture devices, where the at least two image capture devices capture the set of image data from at least two positions.

Still further embodiments relate to tangible, non-transitory computer-readable mediums having stored thereon instructions that cause a processor to execute a method, the method including: obtaining image information of an organism including a set of optical data; calculating a growth index based on the set of optical data; and calculating an anticipated harvest time based on the growth index, where the image information includes at least one of: (a) visible image data obtained from an image sensor and non-visible image data obtained from the image sensor, and (b) a set of image data from at least two image capture devices, where the at least two image capture devices capture the set of image data from at least two positions.

As used herein in various illustrative embodiments, the terms "produce" and "agricultural produce" include organisms. An organism is any living system. The living system may be biologically contiguous.

A further definition of organism, as used herein, is an assembly of molecules functioning as a more or less stable whole that exhibits the properties of life, which includes any living structure capable of growth. Thus, for example, an organism includes, but is not limited to, an animal, fungus, micro-organism, and plant.

Therefore, the terms "produce" and variations thereof, including but not limited to "agricultural produce," as used herein, include but are not limited to animals such as cows, goats, sheep, pigs, fish, and poultry.

Accordingly, for example, the terms "growth index" and variations thereof, including but not limited to "growth state information," "growth situation information," include but are not limited to growth of organisms, including produce and animals.

In addition, for example, the terms "harvest" and variations thereof, including but not limited to "harvesting," "harvest time information," "anticipated proper harvest time," "harvest plan," "harvest plan information," "harvest start time," "harvest time," and "harvest time limit," refer to harvesting of organisms. In various illustrative embodiments, harvesting includes any gathering of mature organisms including produce and/or animals.

Thus, the term "evaluating a growth situation" and variations thereof, as used herein, includes evaluating a growth situation of organisms such as animals and produce. Such evaluation may use various properties of the animals and produce, including a growth index and other properties not listed explicitly herein.

Methods and systems disclosed herein may use optical data. For example, a set of optical data may be used to obtain growth information or a growth index. The optical data may include captured image data including visible and non-visible image data.

As used herein, the term "visible image data" may include image data using a red-green-blue (also referred to as RGB) color model. For example, digital cameras and video cameras often use a particular RGB color space.

As used herein, the term "non-visible image data" may include near-infrared rays (hereinafter, also referred to as NIR).

As used herein, the term "outside parties" and variations thereof, includes general consumers, retailers, restaurants, and food producers. For example, outside parties may include any person or business related to the supply chain system.

An image capture device, as used in various illustrative embodiments disclosed herein, is a device that captures image data or image information. For example, an image capture device may include, but is not limited to, optical devices that store and/or transmit still or moving image data such as a camera or a video camera.

The term "sensor camera" and variations thereof, as used herein, refers to a device that captures images. Sensor cameras may have various functionalities, such as the ability to collect, send, and/or store various properties. Such properties may include but are not limited to information related to growth, temperature, humidity, and atmospheric pressure.

In addition, sensor cameras may have the functionality to transfer information or data over a network or to an external device. For example, the sensor cameras may supply information, including captured image data, to a server.

In the description herein, for the purposes of illustration, methods may be described in a particular order. It should be appreciated that in alternate embodiments, the methods may be performed in a different order than that described. It should also be appreciated that the methods described herein may be performed by hardware components or may be embodied in sequences of machine-executable instructions, which may be used to cause a machine, such as a general-purpose or special-purpose processor (GPU or CPU) or logic circuits programmed with the instructions to perform the methods (FPGA). These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details are given in the description to provide a thorough understanding of the embodiments. However, it will be understood by one of ordinary skill in the art that the illustrative embodiments may be practiced without these specific details.

For example, in some instances, well-known circuits, processes, algorithms, structures, and techniques may be shown or discussed without unnecessary detail in order to avoid obscuring the illustrative embodiments.

Also, it is noted that the embodiments are described as various processes which may be depicted as a flowchart, a flow diagram, a data flow diagram, a structure diagram, or a block diagram, among others. Although any of these depictions may describe various parts of the operations as a sequential process or sequential processes, many of the operations or parts of the operations can be performed in parallel, concurrently, and or redundantly.

In addition, the order of the operations may be rearranged. A process is terminated when its operations are completed, but could have additional steps or repetitive steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, firmware, middleware, microcode, and hardware description languages, among others, or any combination thereof. When implemented in software, firmware, middleware or microcode, the program code or code segments to perform the necessary tasks may be stored in a machine readable medium such as a storage medium.

A processor (s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While illustrative embodiments of the disclosure have been described in detail herein, it is to be understood that the inventive concepts may be otherwise variously embodied and employed, and that the appended claims are intended to be construed to include such variations, except as limited by the prior art.

Advantageous Effects of Invention

According to the embodiments of the presently disclosed technology, a growth index and an anticipated proper harvest time of agricultural produce can be computed. In various embodiments, the computation of the growth index and the anticipated proper harvest time can be improved over prior art computations.

BRIEF DESCRIPTION OF DRAWINGS

FIG. 6 is an illustrative diagram showing a configuration example of management information according to various embodiments of the presently disclosed technology.

DESCRIPTION OF ILLUSTRATIVE EMBODIMENTS

Hereinafter, various illustrative embodiments for the present disclosure (hereinafter, referred to as embodiments) will be described. Note that description will be provided in the following order.

1. First embodiment (Configuration example of an embodiment of an information processing system)
2. First modification example (First modification example of a sensor structure)
3. Second modification example (Second modification example of the sensor structure)
4. Third modification example (Third modification example of the sensor structure)
5. Fourth modification example (Fourth modification example of the sensor structure)

1. First Embodiment

[Configuration Example of an Information Processing System]

First, with reference to FIG. 1, a configuration example of an information processing system that is an illustrative configuration example of various embodiments of the presently disclosed technology will be described.

Figure 1:
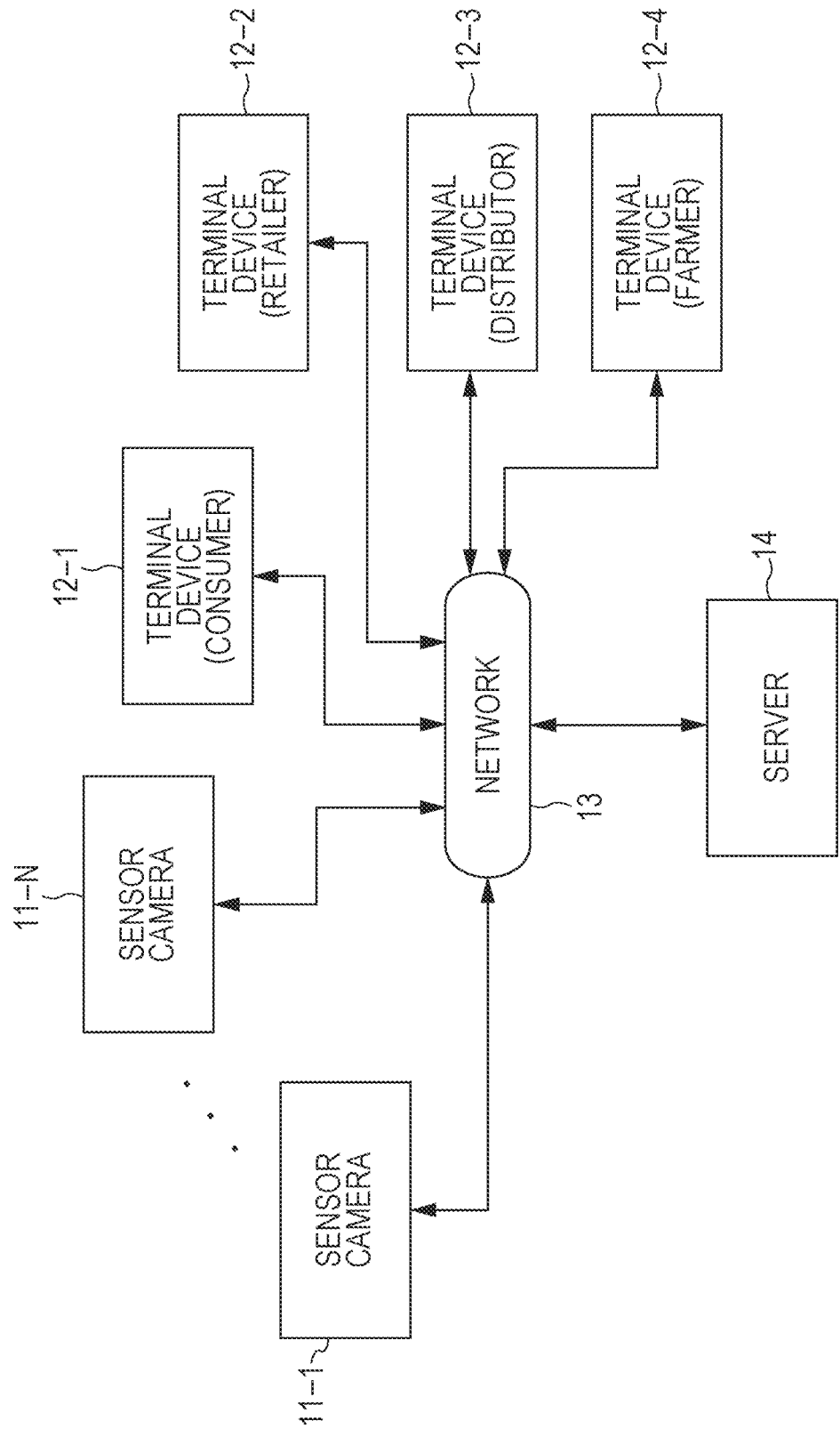
FIG. 1 is an illustrative diagram showing a configuration example of an information processing system according to various embodiments of the presently disclosed technology.

The information processing system of FIG. 1 is configured to include sensor cameras 11-1 to 11-N, terminal devices 12-1 to 12-4 each managed by a consumer, a retailer, a distributor, and a farmer, a network 13, and a server 14. In the information processing system of FIG. 1, images captured by the sensor cameras 11-1 to 11-N are supplied to the server 14 via the network 13 represented by the Internet, and thereby the server 14 computes a growth index of agricultural produce and computes an anticipated proper harvest time based on the growth index. In addition, the server 14 responds to inquiries such as an anticipated proper harvest time from the terminal devices 12-1 to 12-4 each managed by the consumer, the retailer, the distributor, and the farmer, among other outside parties.

In more detail, the sensor cameras 11-1 to 11-N are disposed so that an entire farmland can be imaged at predetermined intervals of the farmland for agricultural produce to be managed (or so that regions that can be proximate to the entire farmland can be imaged by the sensor cameras 11-1 to 11-N as a whole), images that include RGB pixels and pixels of NIR are captured, and the captured image data is transmitted to the server 14 via the network 13. In addition, the sensor cameras 11 measure information of temperature, humidity, and atmospheric pressure, among others, as environment information, and supply the information as well as the captured image data to the server 14 as growth state information. Note that the sensor cameras 11-1 to 11-N are referred to simply as the sensor cameras 11 unless specified otherwise in this and other configurations.

The terminal devices 12-1 to 12-4 are information processing devices configured as, for example, personal computers, among others (also including mobile terminals such as so-called smartphones) managed respectively by a consumer, a retailer, a distributor, and a farmer, and make inquiries of information of a growth index and an anticipated proper harvest time, among others, via the network 13, and receive and display response information to the inquires with respect to the server 14.

The server 14 acquires and accumulates the growth situation information based on the image data, and other information supplied from the sensor cameras 11, and computes a growth index and an anticipated proper harvest time based on the image data. In addition, the server 14 also uses growth situation information of the past in addition to the image data supplied from the sensor cameras 11 to compute an anticipated proper harvest time. Further, when the anticipated proper harvest time computed based on the growth situation information comes, the server 14 notifies the terminal devices 12-1 to 12-4 managed respectively by the consumer, the retailer, the distributor, and the farmer of the information that the anticipated proper harvest time has come via the network 13. Note that the anticipated proper harvest time may be an anticipated date as a proper day to start harvesting, or a day prior by a predetermined number of days from the anticipated date, or for a predetermined number of days from the day prior by a few days from the anticipated date.

[Configuration Example for Realizing a Function of the Sensor Cameras]

Figure 2:
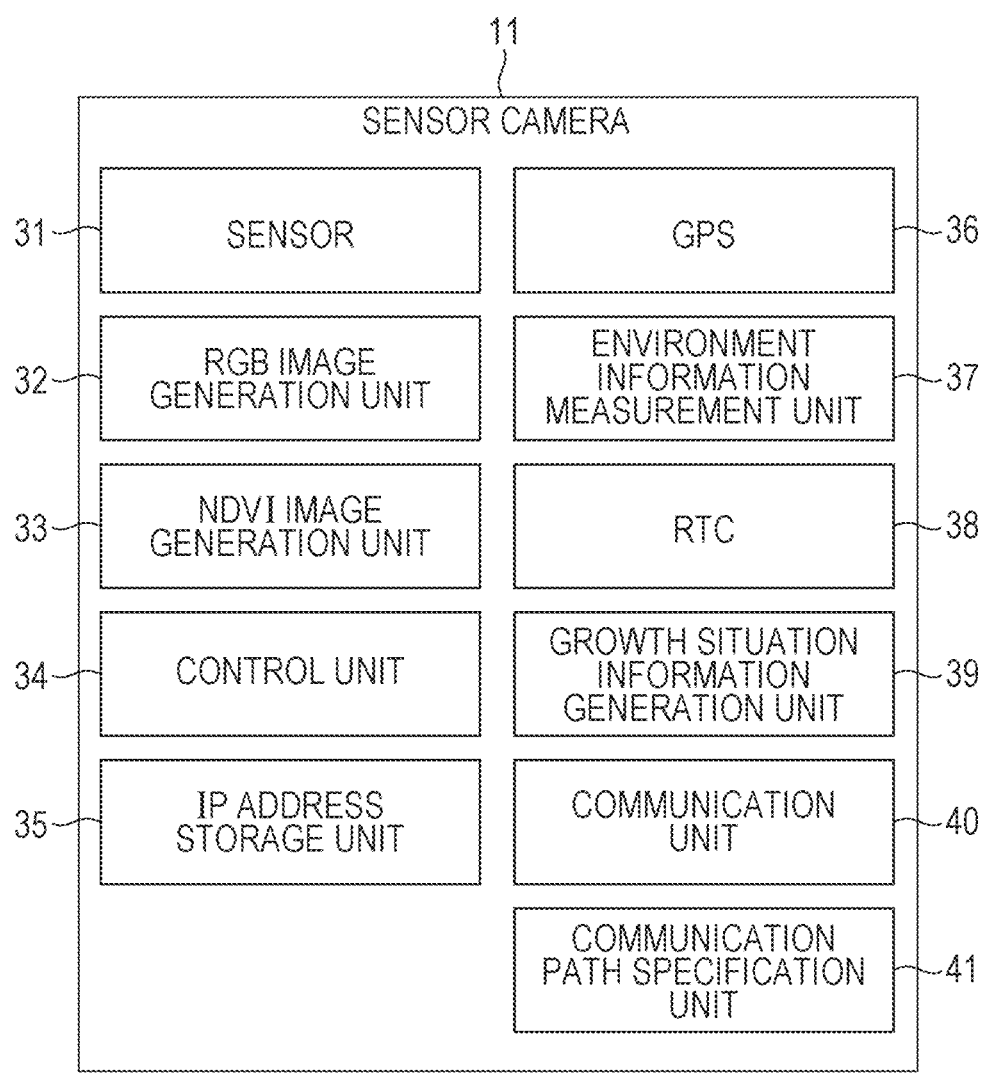
FIG. 2 is an illustrative diagram showing a configuration example of a sensor camera of FIG. 1 according to various embodiments of the presently disclosed technology.

Regarding FIG. 2, an illustrative configuration example for realizing a function of the sensor cameras 11 will be described.

Figure 3:
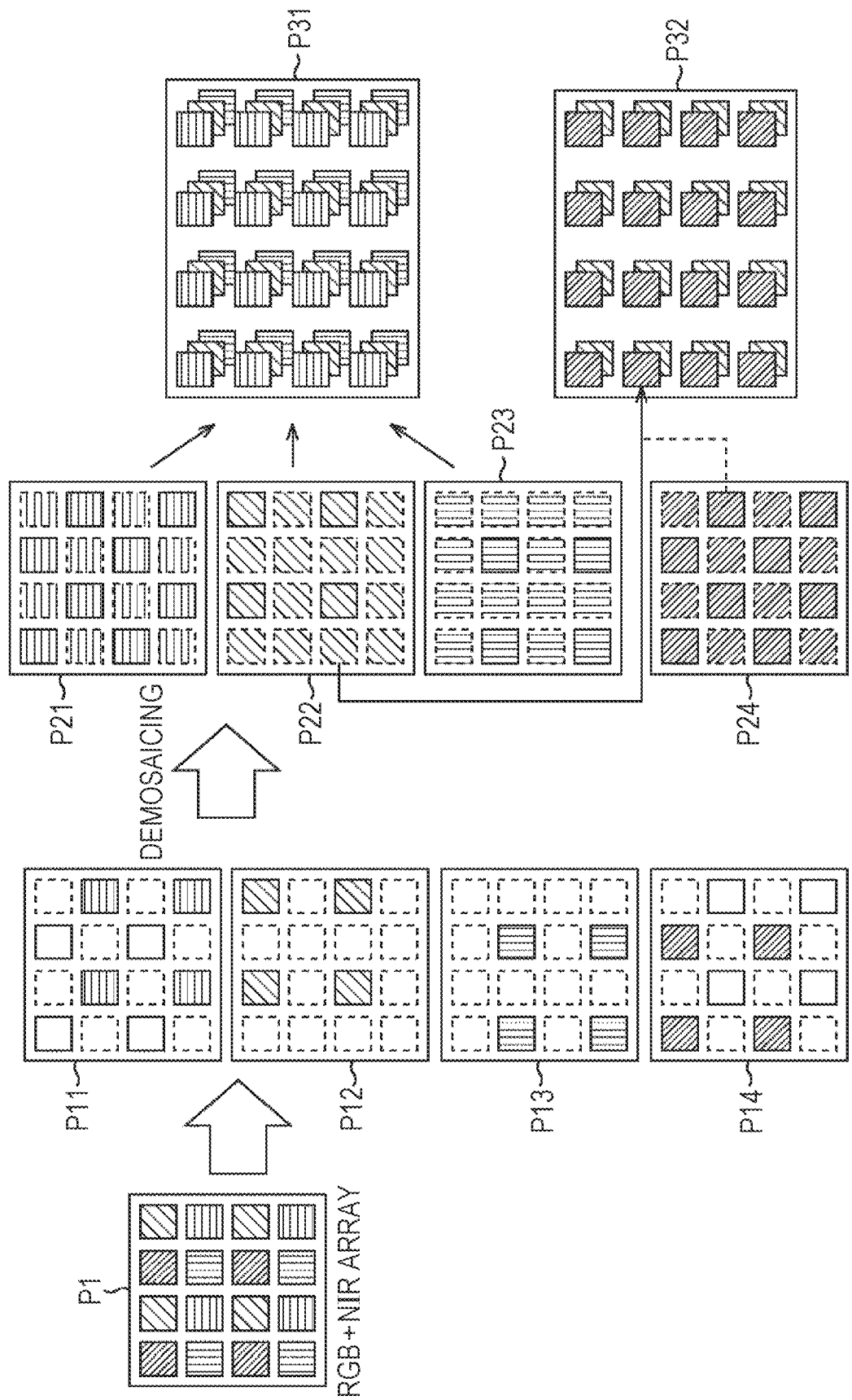
FIG. 3 is an illustrative diagram showing a configuration example of a sensor in the sensor camera of FIG. 2 according to various embodiments of the presently disclosed technology.

Each sensor camera 11 is provided with a sensor 31, an RGB image generation unit 32, an NDVI image generation unit 33, a control unit 34, an IP address storage unit 35, a GPS 36, an environment information measurement unit 37, an RTC 38, a growth situation information generation unit 39, a communication unit 40, and a communication path specification unit 41. The sensor 31 is configured as, for example an image sensor, and has a pixel array as illustrated in, for example, FIG. 3. In other words, in the pixel array of the sensor 31, any of green arrays in a Bayer array composed of general RGB (red, green, and blue) as shown in an image P1 is constituted by near-infrared ray pixels. Note that, in following drawings, the horizontally-striped pattern indicates green, the vertically-striped pattern indicates blue, the upward-shaded part indicates red, and the downward-shaded part indicates near-infrared rays.

The RGB image generation unit 32 generates an RGB image from image signals captured by the sensor 31. In other words, the RGB image generation unit 32 extracts signals of green, red, and blue based on the image signals captured by the sensor 31 with the pixel arrays as shown in the image P1 of FIG. 3 as shown respectively by images P11 to P13, and thereby generates component signal images of green, red, and blue as shown by images P21 to P23 by demosaicing the signals. Further, the RGB image generation unit 32 generates an RGB image as shown by an image P31 by forming the RGB component signal images as shown by the images P21 to P23.

The Normalized Difference Vegetation Index (NDVI) image generation unit 33 generates NIR images from signals of an image captured by the sensor 31. In other words, the NDVI image generation unit 33 extracts NIR signals as shown by an image P14 based on the signals of the image captured by the sensor 31 with the pixel arrays as shown by the image P1 of FIG. 3, and thereby generates an NIR component signal image as shown by an image P24. Furthermore, the NDVI image generation unit 33 generates an NDVI image based on the NIR component signal image and a red component signal image generated by the RGB image generation unit 32 described above. Note that the Normalized Difference Vegetation Index (NDVI) will be described later in detail.

The control unit 34 is constituted by, for example, a microprocessor, a memory, and the like, executes various processes by performing programs stored in the memory, and accordingly controls the entire operations of the sensor cameras 11.

The Internet Protocol (IP) address storage unit 35 stores IP addresses which are information for individually identifying the sensor cameras 11, and may supply the information of the IP addresses to the control unit 34. The Global Positioning System (GPS) 36 receives radio waves from satellites not shown in the drawings, computes positional information such as the longitude and the latitude of the earth in which the sensor cameras 11 are installed, and supplies the information to the control unit 34. The environment information measurement unit 37 measures information of temperature, humidity, and atmospheric pressure, among others as information on the environment in which the sensor cameras 11 are installed, and supplies the information to the control unit 34. The unit includes a Real Time Clock (RTC), and generates time information at all times and supplies the information to the control unit 34. Note that, here, the example in which IP addresses are used as information for individually identifying the sensor cameras 11 is described, however, as information that can individually identify the sensor cameras 11, information other than the IP addresses may be used.

When the sensor 31 captures an image, the growth situation information generation unit 39 generates growth situation information that includes the IP addresses, the RGB image, the NDVI image, the positional information, and the environment information together with time information of the capturing timing. Note that information other than the IP addresses, the RGB image, the NDVI image, the positional information, and the environment information may be included in the growth situation information as long as a growth situation can be checked with the information.

The communication unit 40 is a unit that performs wired or wireless communication via the network 13 such as the Internet, including, for example, an Ethernet board, among others, and controlled by the control unit 34 to transmit the growth situation information to the server 14. The communication path specification unit 41 specifies a communication path during transmission of the growth situation information by the communication unit 40. In other words, the communication path specification unit 41 transmits the growth situation information, which is to be supplied to the server 14 by numerous sensor cameras 11, to the server 14 in the form of sequential relaying between the sensor cameras 11. In other words, when growth situation information of each of the sensor cameras 11-1 to 11-3 is transmitted, the sensor camera 11-1 transmits its growth situation information to the sensor camera 11-2, and the sensor camera 11-2 supplies the growth situation information supplied from the sensor camera 11-1 and its own growth situation information to the sensor camera 11-3. Furthermore, the sensor camera 11-3 supplies the growth situation information of the sensor cameras 11-1 and 11-2 and its own growth situation information to the server 14. In order to perform the communication, the communication path specification unit 41 specifies a communication path by deciding which sensor cameras 11 should be passed through to transmit a sensor camera's growth situation information. As one illustrative specific example, when a communication path specification unit 41 of a sensor camera 11 communicates with a communication path specification unit 41 of a near sensor camera 11 through a communication unit 40 and captures images together that make a pair in order to constitute, for example, a stereoscopic image to be described later, either sensor camera sets and specifies a path so as to transmit growth situation information. With this process, complexity in terms of the communication path can be reduced, and a communication speed can improve. This form of communication may be the same as near field communication represented by, for example, Zigbee (registered trademark). Note that, a communication path may be useful if growth situation information pieces can be sequentially transmitted on the path to the server 14 with improved efficiency, the form of relaying described above being a mere example, and the information pieces may be transmitted in another form.

[Configuration Example to Realize a Function of Terminal Devices]

Figure 4:
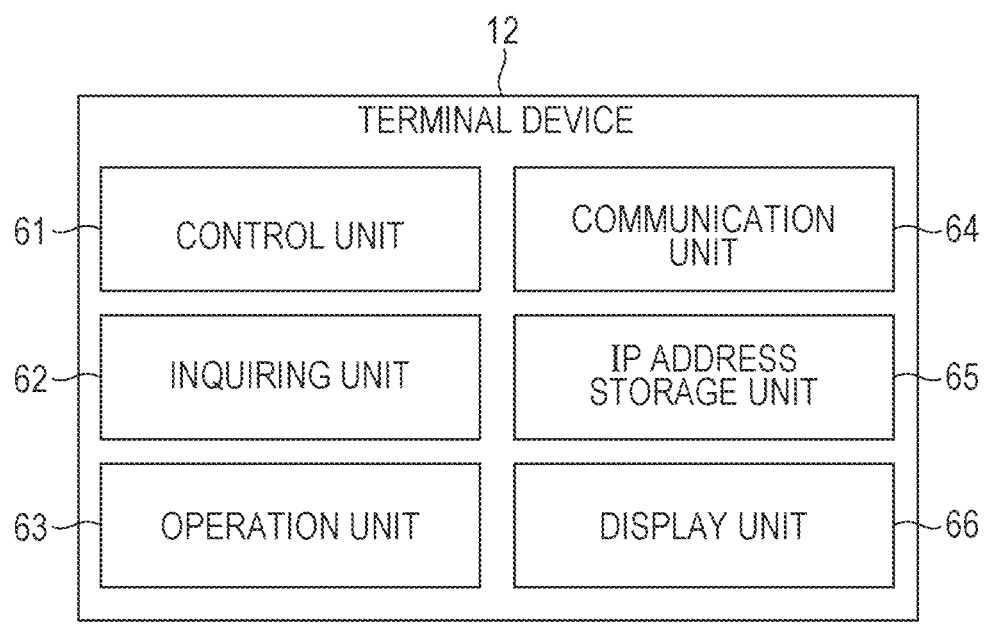
FIG. 4 is an illustrative diagram showing a configuration example of a terminal device of FIG. 1 according to various embodiments of the presently disclosed technology.

Regarding FIG. 4, an illustrative configuration example to realize a function of the terminal devices 12 each managed by the consumer, the retailer, the distributor, and the farmer will be described.

Each of the terminal devices 12 managed by the consumer, the retailer, the distributor, and the farmer is configured to include a control unit 61, an inquiring unit 62, an operation unit 63, a communication unit 64, an IP address storage unit 65, and a display unit 66. The control unit 61 may include a microprocessor and a memory, among other components, and controls entire operations of the terminal device 12 with the microprocessor executing data and programs stored in the memory. When there is an instruction to make an inquiry of all or some of images captured by the sensor cameras 11, a growth index, and an anticipated proper harvest time through an operation of the operation unit 63 that includes a keyboard and a mouse, among others, the inquiring unit 62 controls the communication unit 64 that includes an Ethernet board, for example, such that inquiry information is generated for making an inquiry of images captured by the sensor cameras 11, a growth index, and an anticipated proper harvest time to the server 14 together with information of IP addresses for specifying the sensor cameras 11 which is stored in the IP address storage unit 65 and managed by the inquiring unit itself (or of which the inquiring unit desires to make an inquiry). The inquiring unit 62 transmits the generated inquiry information to the server 14 using the communication unit 64. In addition, the communication unit 64 receives response information transmitted from the server 14 in response to the inquiry information and supplies the information to the control unit 61. The control unit 61 causes the display unit 66 that includes a Liquid Crystal Display (LCD), and an organic EL (Electro Luminescence), among others, to display the response information.

[Configuration Example to Realize a Function of the Server]

Figure 5:
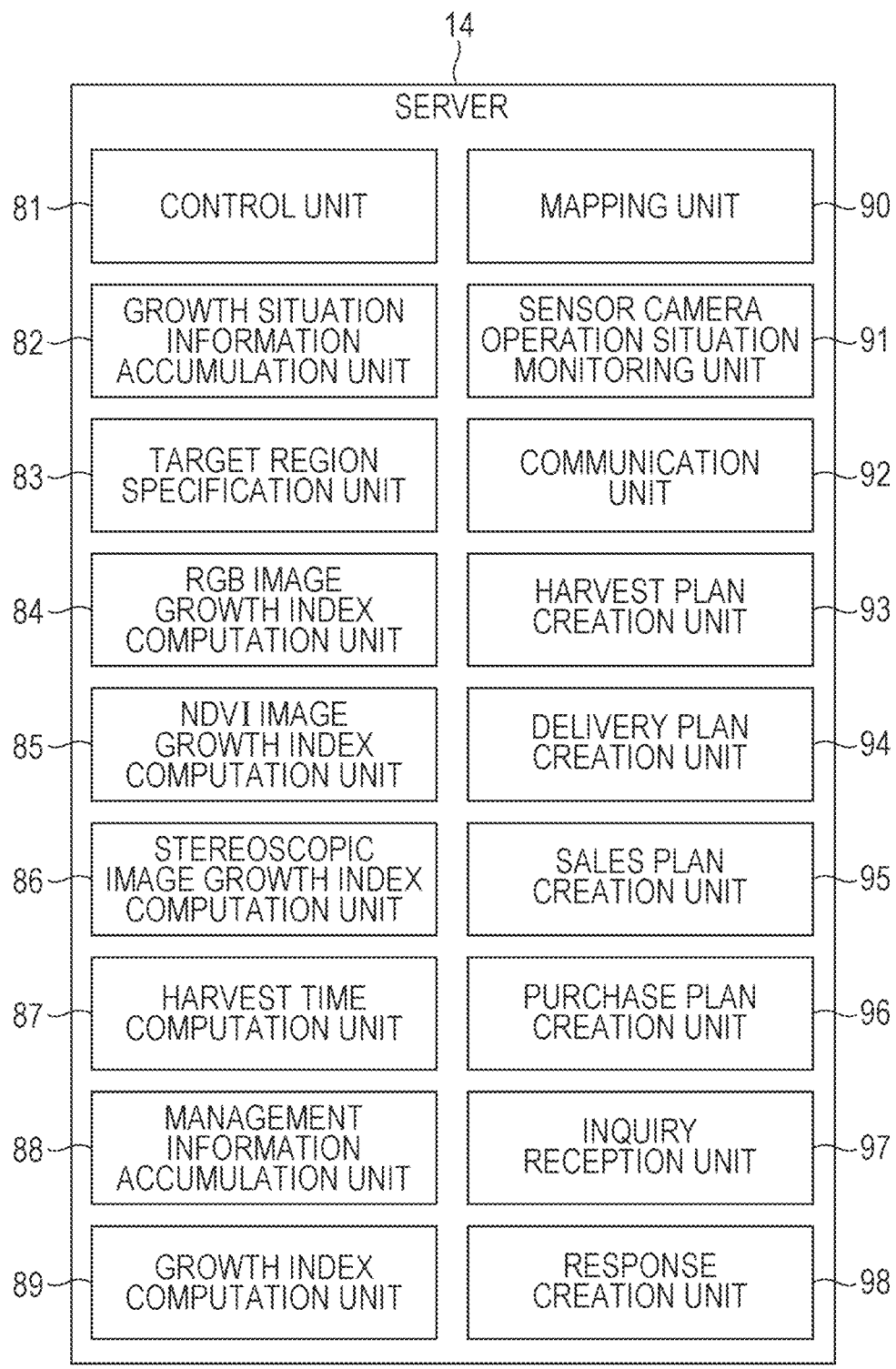
FIG. 5 is an illustrative diagram showing a configuration example of a server of FIG. 1 according to various embodiments of the presently disclosed technology.

Regarding FIG. 5, an illustrative configuration example to realize a function of the server 14 will be described.

The server 14 is configured to include a control unit 81, a growth situation information accumulation unit 82, a target region specification unit 83, an RGB image growth index computation unit 84, an NDVI image growth index computation unit 85, a stereoscopic image growth index computation unit 86, a harvest time computation unit 87, a management information accumulation unit 88, a growth index computation unit 89, a mapping unit 90, a sensor camera operation situation monitoring unit 91, a communication unit 92, a harvest plan creation unit 93, a delivery plan creation unit 94, a sales plan creation unit 95, a purchase plan creation unit 96, an inquiry reception unit 97, and a response creation unit 98.

The control unit 81 may include a microprocessor, a memory, and the like, and controls entire operations of the server 14 by executing data and programs stored in the memory.

The growth situation information accumulation unit 82 stores growth situation information supplied from the sensor cameras 11 via the communication unit 92 in association with IP addresses used to identify the sensor cameras 11.

The target region specification unit 83 specifies a region within an image in which agricultural produce to be monitored is present based on an RGB image included in growth situation information. As one illustrative specific example, the target region specification unit 83 stores patterns of colors and shapes serving as characteristic information of each agricultural produce, and specifies a target region by searching for a region that matches the characteristic information within the RGB image. Note that, here, the target region specification unit 83 being described provided in the server 14, may, however, be provided in each sensor camera 11 so that, for example, information of the target region is included in growth situation information. In addition, since the target region specification unit 83 has only to be able to specify a target region, the target region specification unit may specify a target region only using an image other than an RGB image, for example, an NIR image.

The RGB image growth index computation unit 84 computes a growth index based on information of an image region specified as a target region out of an RGB image. For example, since the time in which a ratio of green accounting for a rice hull in one ear is about 10% is set to be a harvest start time, and the time in which a ratio thereof is about 2% is set to be a harvest time limit, the RGB image growth index computation unit 84 computes a growth index based on the ratios of green of rice hulls. Since the RGB image growth index computation unit 84 computes an RGB image growth index only using image information of a region in an RGB image in which a target is present, the RGB image growth index computation unit 84 can compute the growth index with higher accuracy.

The NDVI image growth index computation unit 85 computes a growth index based on information of an image region specified as a target region in an NDVI image. Here, an NDVI indicates a normalized vegetation index as expressed by the following formula (1).

$$NDVI=(R\_NIR-R\_RED)/(R\_NIR+R\_RED) \quad (1)$$

In formula (1), NDVI is a normalized vegetation index, R_NIR is the reflectance of near-infrared light, and R_RED is the reflectance of red light. Thus, the NDVI image generation unit 33 of the sensor camera 11 described above generates an image obtained from an arithmetic operation of the above-described formula (1) as an NDVI image. An NDVI is used as an index of growth of foliage. Note that the reflectances of near-infrared light and red light are computed by obtaining red light intensity and NIR intensity in a region that is not a target region, for example, the sky as incident light intensity, and obtaining red light intensity and NIR intensity in a target region as reflected light intensity in an RGB image and an NIR image. In addition, the reflectances of near-infrared light and red light may also be obtained by measuring intensity of incident light with reference to a diffuser panel having a known reflectance, calculating a reflection coefficient from a ratio between the intensity and reflection luminance of a target, and converting the coefficient to a reflectance. Furthermore, the NDVI image growth index computation unit 85 computes an NDVI image growth index from the average value, the variance, or the high-order variance of an NDVI only of a target region. With the operation, the NDVI image growth index is computed only from information obtained from pixels within the target region, and the NDVI image growth index can be computed with higher accuracy.

The stereoscopic image growth index computation unit 86 generates a parallax image based on information of regions of the same target captured by the plurality of sensor cameras 11, acquires sizes of target agricultural produce as stereoscopic information, and computes a stereoscopic image growth index based on image information that includes the stereoscopic sizes.

The harvest time computation unit 87 computes an anticipated proper harvest time based on an RGB growth index, an NDVI growth index, a stereoscopic image growth index, and past information of the information of the aforementioned elements accumulated in the growth situation information accumulation unit 82.

The management information accumulation unit 88 stores information of a sensor position, a region (a country, a city, etc.), the type of agricultural produce, the owner of agricultural produce (or a farm), a farm or field Gp, a contract distributor, a contract retailer, a group, a growth index, and an anticipated proper harvest time for each IP address for identifying the sensor cameras 11 as shown in FIG. 6. In the field of the sensor position, information acquired by the GPSs 36 provided in the sensor cameras 11 is registered. In the field of a region, a country, a city, etc. set in association with a sensor position is registered. In the field of the type of agricultural produce, information indicating the type of agricultural produce cultivated in a cultivation area monitored by the sensor cameras 11 is registered. In the field of the owner of agricultural produce (or a farm), information of the owner of agricultural produce or a farm for which the sensor cameras 11 specified by IP addresses are installed is registered. In the field of the farm or field Gp, a group, etc. managed by, for example, the same owner is registered. In the field of the contract distributor, information of a distributor who will transport agricultural produce monitored by the sensor cameras 11 which are identified by the IP addresses is registered. In the field of the contract retailer, information of a contract retailer who will sell the agricultural produce monitored by the sensor cameras 11 which are identified by the IP addresses is registered. In the field of the group, a group name allotted to regions in which harvesting is performed at the same time is registered. In the field of growth index, a growth index of the agricultural produce within the range monitored by the sensor cameras 11 which are identified by the IP addresses is registered. In the field of the anticipated proper harvest time, information of an anticipated proper harvest time that is anticipated based on the growth index and past information thereof is registered.

In FIG. 6, AAA, BBB, and CCC are registered as IP addresses. In addition, a sensor position with an IP address of AAA is indicated by A, the region by a, the type of agricultural produce by Alpha, the owner of agricultural produce by "Kou," the farm or field Gp by G1, the contract distributor by (1), the contract retailer by "Ah," the group by i, the growth index by 60, and the anticipated proper harvest time by October 15.

In a similar manner, a sensor position with an IP address of BBB is indicated by B, the region by a, the type of agricultural produce by Alpha, the owner of agricultural produce by "Kou," the farm or field Gp by G1, the contract distributor by (1), the contract retailer by "Ah," the group by i, the growth index by 70, and the anticipated proper harvest time by October 16.

Furthermore, a sensor position with an IP address of CCC is indicated by C, the region by c, the type of agricultural produce by Beta, the owner of agricultural produce by "Otsu," the farm or field Gp by G2, the contract distributor by (2), the contract retailer by "Eah," the group by ii, the growth index by 65, and the anticipated proper harvest time by October 20.

The growth index computation unit 89 computes a growth index set as, for example, a weighted average of an RGB growth index, an NDVI growth index, and a stereoscopic image growth index based on any one or all of the indexes.

The mapping unit 90 generates information obtained by mapping growth indexes and anticipated proper harvest times as information on maps of each region.

When the sensor camera operation situation monitoring unit 91 compares time-series changes of RGB images included in growth situation information and there are extremely drastic changes, the sensor camera operation situation monitoring unit monitors operation situations by determining whether or not there is an abnormal operation state occurring in the sensor cameras 11.

The communication unit 92 may include an Ethernet board, and the like, and is controlled by the control unit 81, thereby receiving the growth situation information and the inquiry information transmitted from the terminal devices 12 and transmitting response information to the terminal devices 12.

The harvest plan creation unit 93 generates harvest plan information from harvest time information based on the growth situation information and anticipated proper harvest time information, and transmits the information to the terminal device 12 managed and operated by the farmer by using the communication unit 92. Note that the harvest plan information may be transmitted not only to the terminal device 12 managed and operated by the farmer but also to the terminal devices 12 managed and operated by the distributor, the retailer, and the consumer. Owing to the transmission, the distributor, the retailer, and the consumer also can formulate their own distribution plans, sales plans, and purchase plans from the harvest plan information.

The delivery plan creation unit 94 generates delivery plan information from the harvest time information based on the growth situation information and the anticipated proper harvest time information, and transmits the information to the terminal device 12 managed and operated by the distributor by using the communication unit 92.

The sales plan creation unit 95 generates sales plan information from the harvest time information based on the growth situation information and the anticipated proper harvest time information, and transmits the information to the terminal device 12 managed and operated by the retailer by using the communication unit 92.

The purchase plan creation unit 96 generates purchase plan information from the harvest time information based on the growth situation information and the anticipated proper harvest time information, and transmits the information to the terminal device 12 managed and operated by the consumer by using the communication unit 92.

The inquiry reception unit 97 controls the communication unit 92 such that inquiry information is received including inquiries with regard to a harvest time, among other information, transmitted from the terminal devices 12 operated by either of the consumer, the retailer, the distributor, and the farmer, for example, through the network 13.

The response creation unit 98 generates response information including, for example, growth index mapping information generated by the mapping unit 90 corresponding to information received as inquiry information, and controls the communication unit 92 such that the response information is transmitted to the terminal devices 12 that transmitted the inquiry information.

[Growth Situation Information Accumulation Process by a Sensor Camera]

Figure 7:
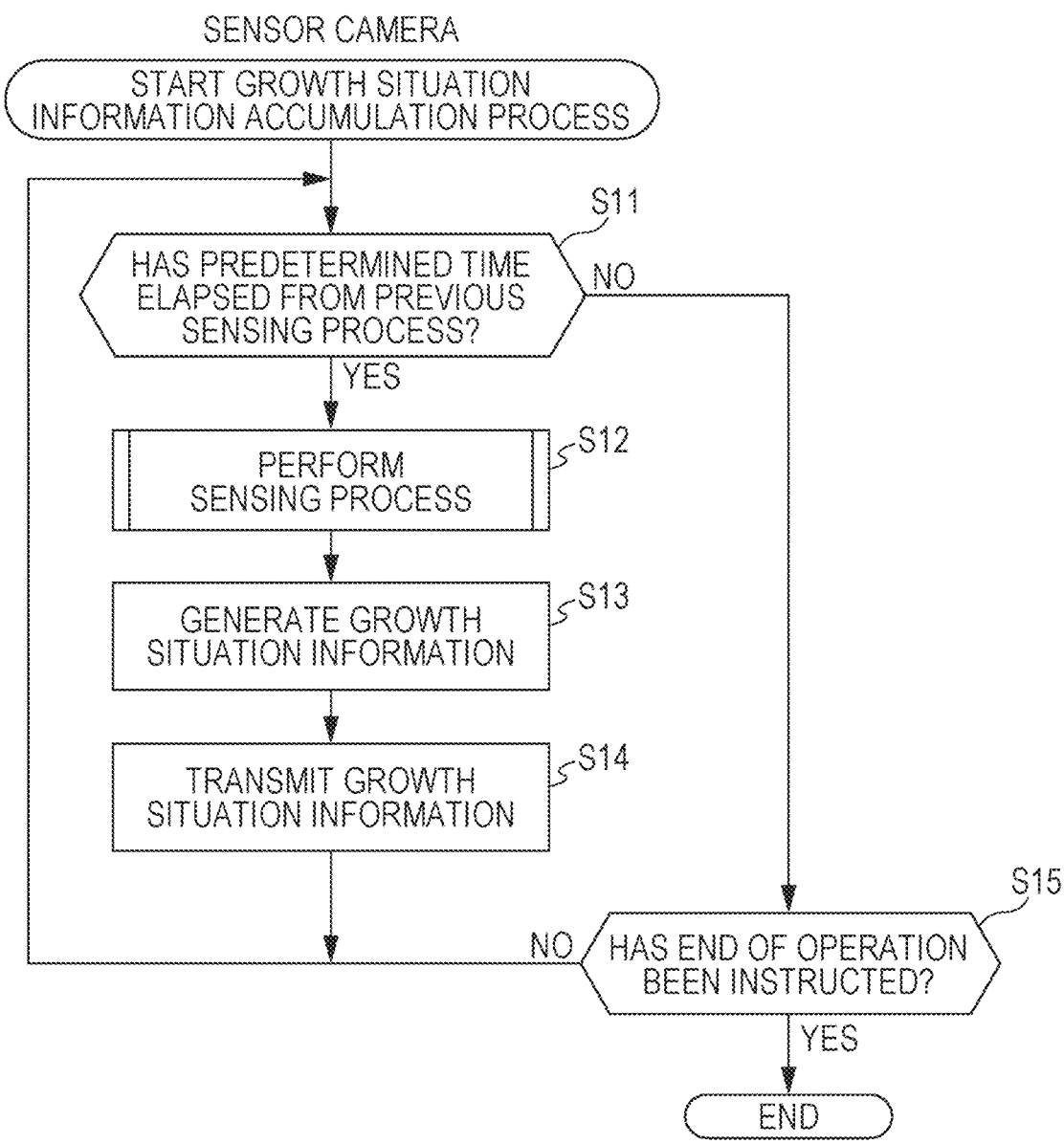
FIG. 7 is an illustrative flowchart for describing a growth situation information accumulation process performed by the sensor camera according to various embodiments of the presently disclosed technology.

Regarding FIG. 7, an illustrative growth situation information accumulation process by a sensor camera 11 will be described.

In Step S11, the control unit 34 of the sensor camera 11 determines whether or not a predetermined time has elapsed from a previous sensing process based on time information generated by the RTC 38 and time information at which the previous sensing process started. When a predetermined time has not elapsed from the previous sensing process in Step S11, the process proceeds to Step S15.

In Step S15, the control unit 34 determines whether or not an end of an operation has been instructed through an operation of an operation unit not shown in the drawings. When an end of the operation is instructed in Step S15, the process ends, and when an end of the operation is not instructed, the process returns to Step S11. In other words, the processes of Steps S11 and S15 are repeated until an end of the operation is instructed or the predetermined time elapses. In addition, when the predetermined time elapses in Step S11, the process proceeds to Step S12.

In Step S12, the sensor 31 executes a sensing process, and acquires an RGB image and an NDVI image from the sensing process. Note that various illustrative embodiments of the sensing process will be described later in detail with reference to the flowchart of FIG. 10.

In Step S13, the growth situation information generation unit 39 generates growth situation information based on the RGB image and the NDVI image acquired from the sensing process, IP addresses stored in the IP address storage unit 35, positional information including longitude and latitude on the earth acquired by the GPS 36, information of temperature, humidity, and atmospheric pressure measured by the environment information measurement unit 37 and the time information generated by the RTC 38. Note that, since the growth situation information has only to include information indicating a growth situation of agricultural produce or information for recognizing the growth situation, the growth situation information may include information indicating a growth situation or information for recognizing the growth situation in addition to the RGB image and the NDVI image, the IP address, the positional information including longitude and latitude on the earth, the information of temperature, humidity, and atmospheric pressure, and the time information.

In Step S14, the control unit 34 controls the communication unit 40 such that the generated growth situation information is transmitted to the server 14, and the process returns to Step S11. At this moment, in various embodiments, the control unit 34 controls the communication path specification unit 41 so as to communicate with a peripheral sensor camera 11, then to specify a sensor camera 11 which will be passed through for transmitting the growth situation information to the server 14, and then to transmit the growth situation information to the server 14 via the specified sensor camera 11 on the communication path.

Figure 8:
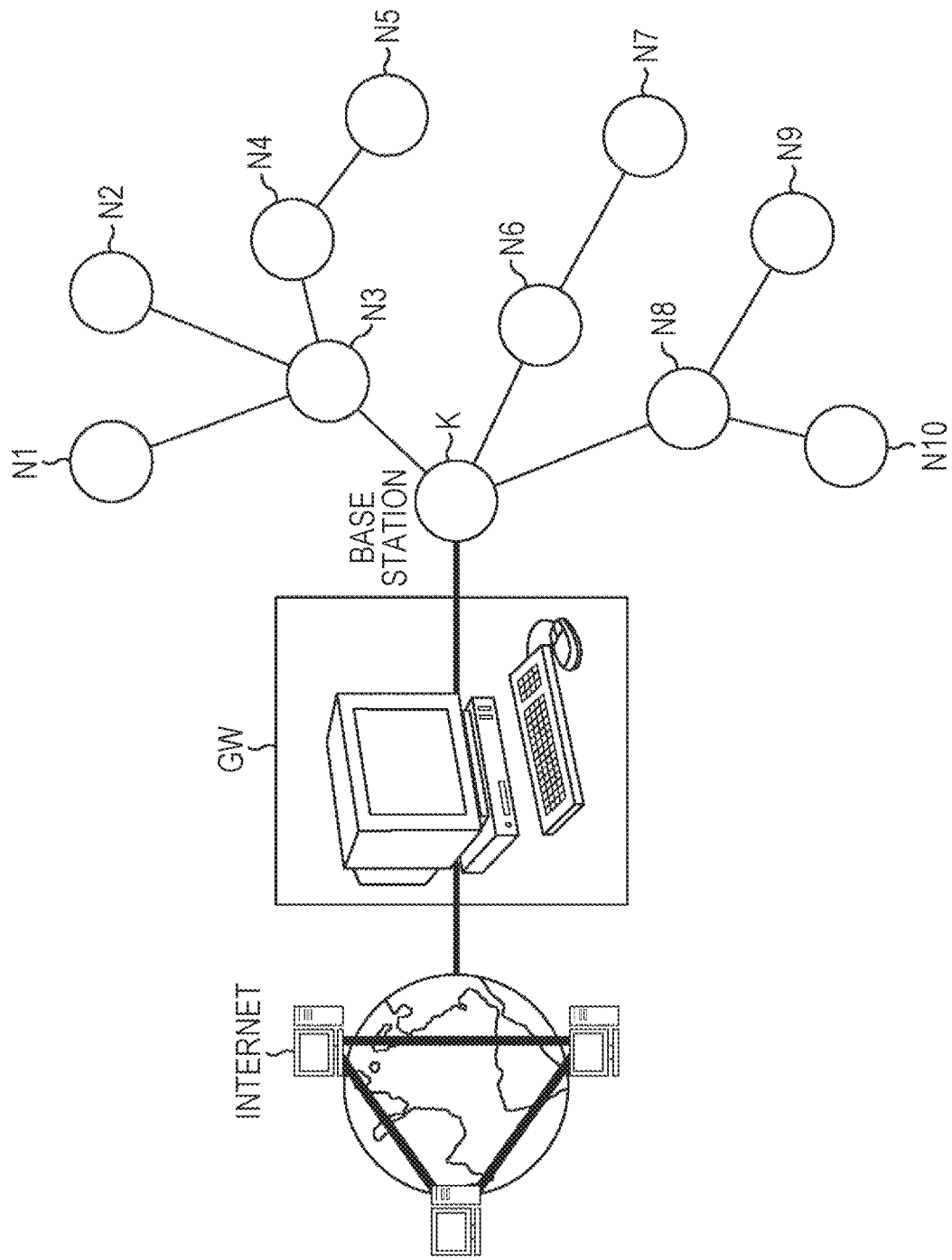
FIG. 8 is an illustrative diagram for describing a transfer method of growth situation information between sensor cameras according to various embodiments of the presently disclosed technology.

In other words, as illustrated in FIG. 8, when positions in which the sensor cameras 11 are installed are indicated by nodes N1 to N10, for example, and information is set to be output to the Internet via a base station K and a gateway GW, growth situation information of the sensor camera 11 corresponding to the node N5 is transferred to the base station K through the sensor camera 11 indicated by the node N4 and the sensor camera 11 indicated by the node N3 which are located nearby. In this illustrative case, the sensor camera 11 indicated by the node N4 transfers the growth situation information of the node N5 and its own growth situation information to the node N3. Furthermore, the nodes N1 and N2 transfer their own growth situation information to the Node N3. In addition, the node N3 rearranges, and transfers to the base station K, the growth situation information from the nodes N1 to N5. In addition, the sensor camera 11 indicated by the node N7 transfers growth situation information to the sensor camera 11 indicated by the node N6, and the sensor camera 11 indicated by the node N6 rearranges the growth situation information of the nodes N6 and N7, and outputs the information to the Internet via the base station K and the gateway GW. Furthermore, the sensor cameras 11 indicated by the nodes N9 and N10 respectively transfer their growth situation information to the sensor camera 11 indicated by the node N8, and the sensor camera 11 indicated by the node N8 rearranges the growth situation information of the nodes N8 to N10, and outputs the information to the Internet via the base station K and the gateway GW.

Due to the above process, complexity caused by communication between the base station K and the gateway GW can be more relieved and the growth situation information can be transferred at a higher speed than when the growth situation information from all sensor cameras 11 is output at one time. Note that since the growth situation information of all sensor cameras 11 has only to be transmitted to the server 14 with efficiency, the growth situation information of all sensor cameras 11 may be transferred using methods other than being relayed as described above, or, for example, may be transferred directly to the base station K from each of the sensor cameras 11. In addition, each of the sensor cameras 11 may rearrange and transfer the growth situation information from another sensor camera 11, or may sequentially transfer each piece of growth situation information to the base station K in a predetermined order. As one example, when each of the sensor cameras 11 transfers the growth situation information directly to the base station K, the information can be transferred from each of the sensor cameras 11 to the base station K, and this may happen with improved efficiency.

Figure 9:
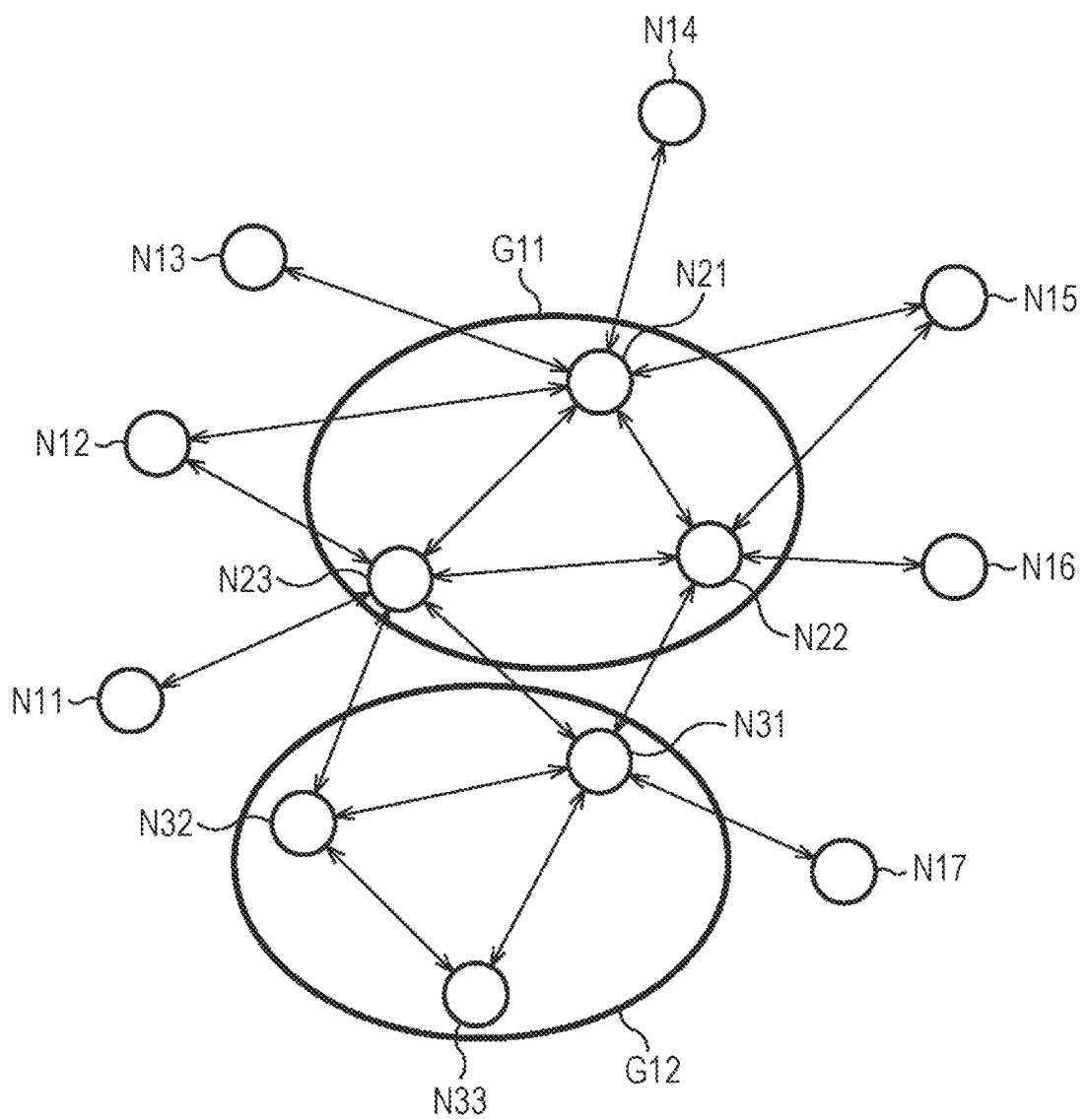
FIG. 9 is an illustrative diagram for describing another transfer method of growth situation information between sensor cameras according to various embodiments of the presently disclosed technology.

In addition, as illustrated in FIG. 9, when sensor cameras 11 indicated by nodes N11 to N17, N21 to N23, and N31 to N33 are installed, it may be configured that, with regard to the sensor cameras 11 indicated by, for example, the nodes N21 to N23 and N31 to N33, the sensor cameras 11 indicated by the nodes N21 to N23 are set to be a first group G11, the sensor cameras 11 indicated by the nodes N31 to N33 are set to be a second group G12, pieces of the growth situation information are collected in a representative node of each group, and the sensor camera 11 of the representative node rearranges and outputs pieces of the growth situation information of the sensor cameras 11 of the other nodes that belong to the group. Further, with regard to setting the groups G11 and G12, for example, sensor cameras 11 present in farmlands owned by the same owner may be set to be in the same group, or sensor cameras 11 paired in order to capture a stereoscopic image described herein may be set to be in the same group.

From the process described above, pieces of the growth situation information that include RGB images and NDVI images can be generated at a predetermined time interval, sequentially transmitted to the server 14, and sequentially accumulated in the server 14.

[Sensing Process]

Figure 10:
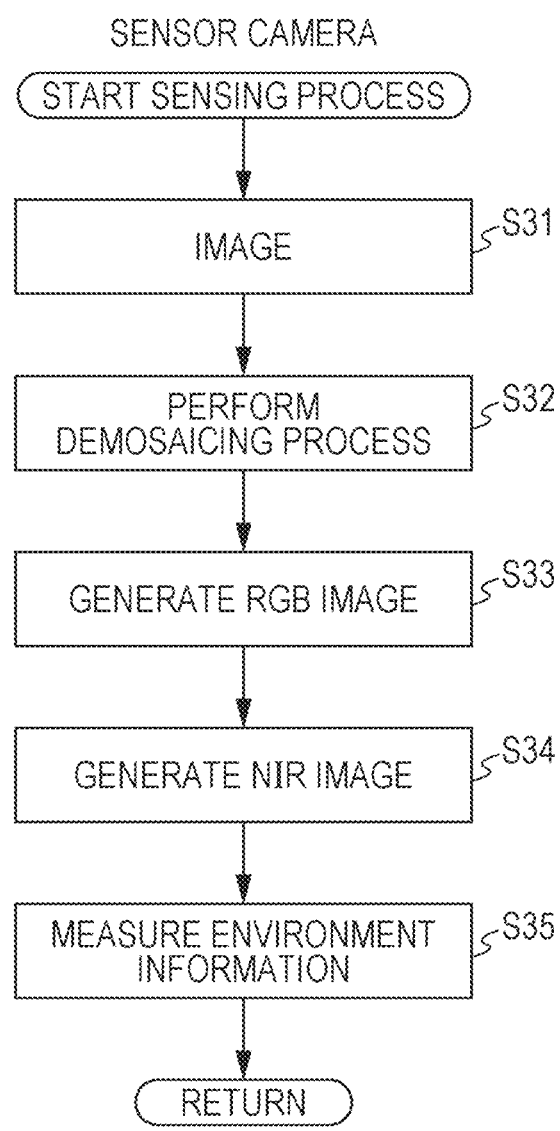
FIG. 10 is an illustrative flowchart for describing a sensing process performed by the sensor camera according to various embodiments of the presently disclosed technology.

Regarding FIG. 10, an illustrative sensing process will be described.

In Step S31, the sensor 31 captures an image having a size in which the size and the color of agricultural produce to be harvested can be fully recognized in a range of cultivation of the produce that is a subject. In addition, the sensor cameras 11 are installed at an interval and in a direction in which imaging of the farmland under the imaging conditions described above can be performed.

In Step S32, the RGB image generation unit 32 and the NDVI image generation unit 33 performs a demosaicing process on light beams of each color of pixels captured by the sensor 31. In other words, the RGB image generation unit 32 performs the demosaicing process on pixels of respective red, green and blue light to generate red, green, and blue component signal images. In addition, the NDVI image generation unit 33 performs a demosaicing process on pixels of NIR to generate an NIR component signal image.

In Step S33, the RGB image generation unit 32 combines the demosaiced RGB component signal images to generate an RGB image.

In Step S34, the NDVI image generation unit 33 measures intensity of NIR and red light serving as light incident from a region recognized as an image of the sky for each pixel and measures intensity of NIR and red light serving as reflected light in regions other than the aforementioned region based on the NIR image and the red image, computes reflectances of the NIR and the red light, and generates an NDVI image. For this reason, the sensor 31 is installed at an angle at which the captured region of the agricultural produce which is a subject and a region in which incident light of red light or NIR from the sky can be measured are included. In addition, when it is difficult to install the sensor at this angle, a panorama and a tilt mechanism are provided in the sensor cameras 11, incident light of red light and NIR are captured with the cameras facing the sky, the cameras are controlled such that regions of the agricultural produce which is a subject are imaged, reflected light is captured, and the NDVI image described above is generated. In addition, the reflectances of the NIR and the red light may also be obtained by measuring intensity of the incident light with reference to a diffuser panel having a known reflectance, calculating a reflection coefficient from a ratio between the intensity and reflection luminance of a target, and converting the coefficient to a reflectance.

In Step S35, the control unit 34 controls the environment information measurement unit 37 such that temperature, humidity, and atmospheric pressure constituting the environment information are measured.

With the process described above, information constituting growth situation information such as the RGB image, the NDVI image, and temperature, humidity, and atmospheric pressure which are included in the measured environment information is generated. Note that the information constituting the growth situation information may include information other than the RGB image, the NDVI image, and temperature, humidity, and atmospheric pressure which are included in the environment information. Such information may include information that is necessary for recognizing a growth situation.

[Growth Situation Information Accumulation Processes by the Server and Each Terminal Device]

Figure 11:
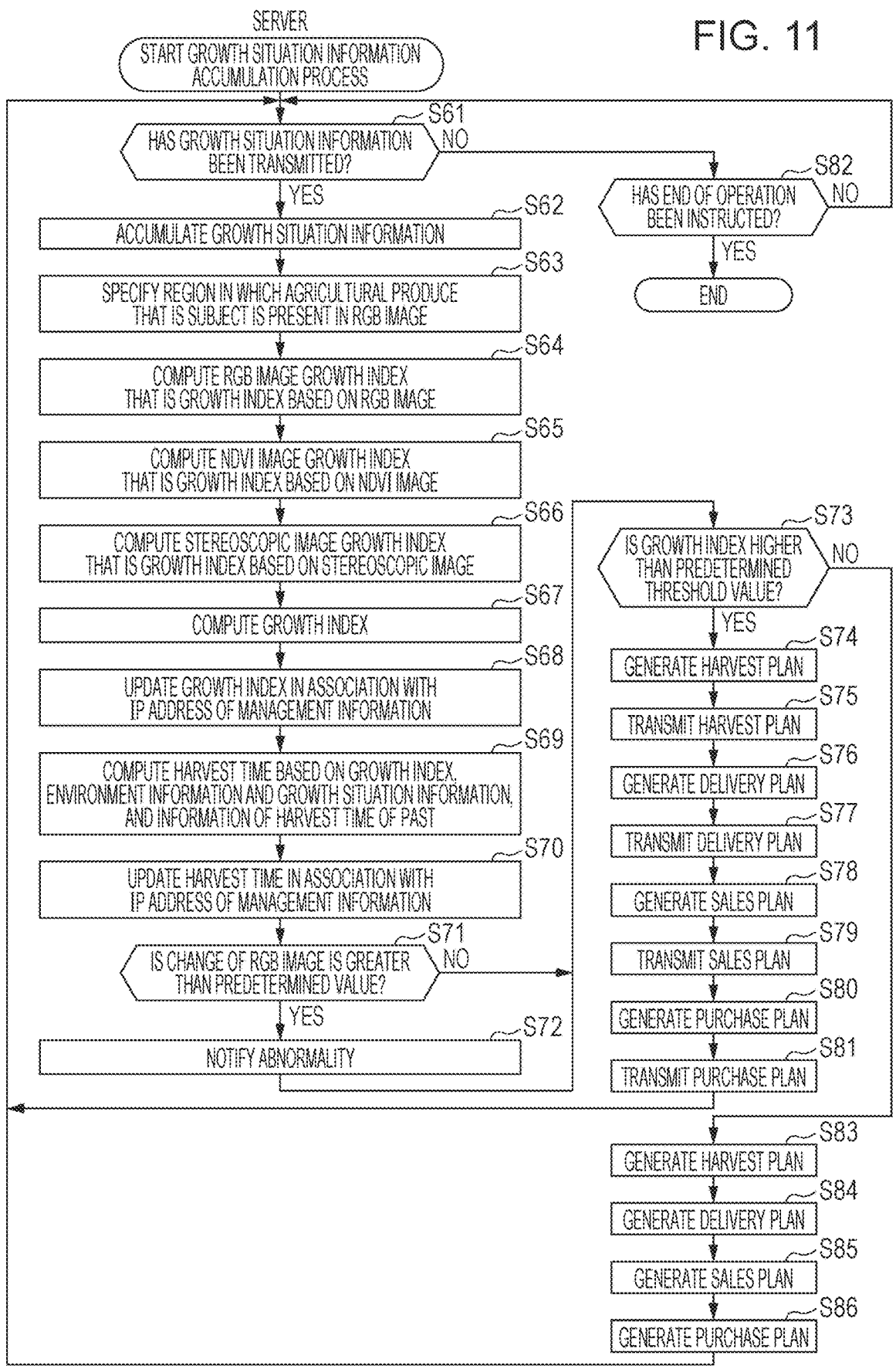
FIG. 11 is an illustrative flowchart for describing the growth situation information accumulation process performed by a server according to various embodiments of the presently disclosed technology.
Figure 12:
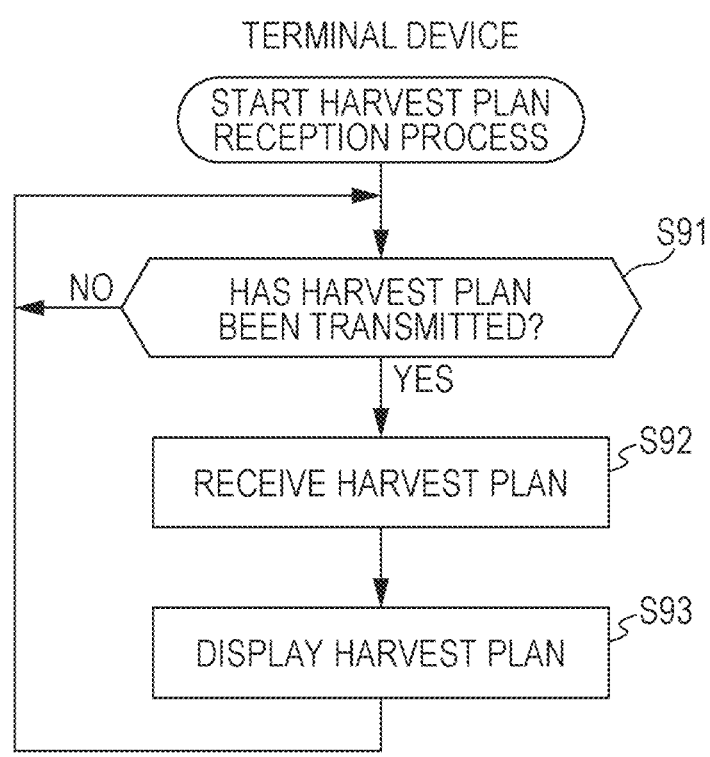
FIG. 12 is an illustrative flowchart for describing a harvest plan reception process performed by the terminal device according to various embodiments of the presently disclosed technology.

Regarding FIGS. 11 and 12, growth situation information accumulation processes by the server 14 and each terminal device 12 will be described.

In Step S61, the control unit 81 of the server 14 controls the communication unit 92 such that whether or not growth situation information has been transmitted from any sensor camera 11 is determined, and when the information is not transmitted, the process proceeds to Step S82.

In Step S82, the control unit 81 determines whether or not an operation unit not shown in the drawings has been operated and an end of an operation has been instructed, and when an end thereof is instructed, the process ends. In addition, when an end thereof is not instructed, the process returns to Step S61. In other words, when an end thereof is not instructed and the growth situation information is not transmitted, the processes of Steps S61 and S82 are repeated. When the growth situation information is transmitted in Step S61 from, for example, the process of Step S14 of FIG. 7, the process proceeds to Step S62.

In Step S62, the control unit 81 controls the communication unit 92 such that the growth situation information transmitted from the sensor cameras 11 is received and controls the growth situation information accumulation unit 82 such that the received growth situation information is accumulated. In this illustrative case, the received growth situation information may be constituted by a plurality of pieces of growth situation information from the plurality of sensor cameras 11 as described herein. Thus, the plurality of pieces of growth situation information may be accumulated through a one-time process. However, in the following description, the whole process proceeds by assuming that pieces of growth situation information are transmitted from two sensor cameras 11, which capture the same target as a stereoscopic image, in one reception process, although other processes are also encompassed by various embodiments of the present disclosure.

In Step S63, the control unit 81 controls the target region specification unit 83 such that a target region that is a region in an image which is obtained by imaging target agricultural produce based on an RGB image included in the transmitted growth situation information is specified. As one illustrative specific example, the target region specification unit 83 extracts feature information such as the shape and the hue of the agricultural produce of which a growth index is to be computed from the RGB image. In addition, the target region specification unit 83 determines whether or not the extracted feature information matches the actual shape and hue of the agricultural produce stored in advance, and specifies a target region that includes the region within the matching RGB image in which the agricultural produce of which a growth index is to be computed is imaged. Note that, in this illustrative case, with regard to the agricultural produce to be specified, for example, the target region specification unit 83 may specify the feature information by searching for the management information accumulated in the management information accumulation unit 88 based on the IP addresses included in the growth situation information including the RGB image, and reading and using the information registered in the field of the type of agricultural produce, as shown in FIG. 6.

In Step S64, the control unit 81 controls the RGB image growth index computation unit 84 such that an RGB image growth index is computed based on the target region in the RGB image. As one illustrative specific example, with regard to a harvest time of rice, for example, the RGB image growth index computation unit 84 assumes the time in which a ratio of green accounting for a rice hull in one ear is about 10% to be a harvest start time, and the time in which a ratio thereof is about 2% to be a harvest time limit, and thus, a growth index is computed based on the ratios of green of rice hulls, and the index is defined as an RGB image growth index.

In Step S65, the control unit 81 controls the NDVI image growth index computation unit 85 such that an NDVI image growth index is computed based on the target region in an NDVI image. As one illustrative specific example, the NDVI image growth index computation unit 85 computes, for example, the average value, the variance, or the high-order variance of an NDVI of the target region, thereby computing the NDVI image growth index.

Figure 13:
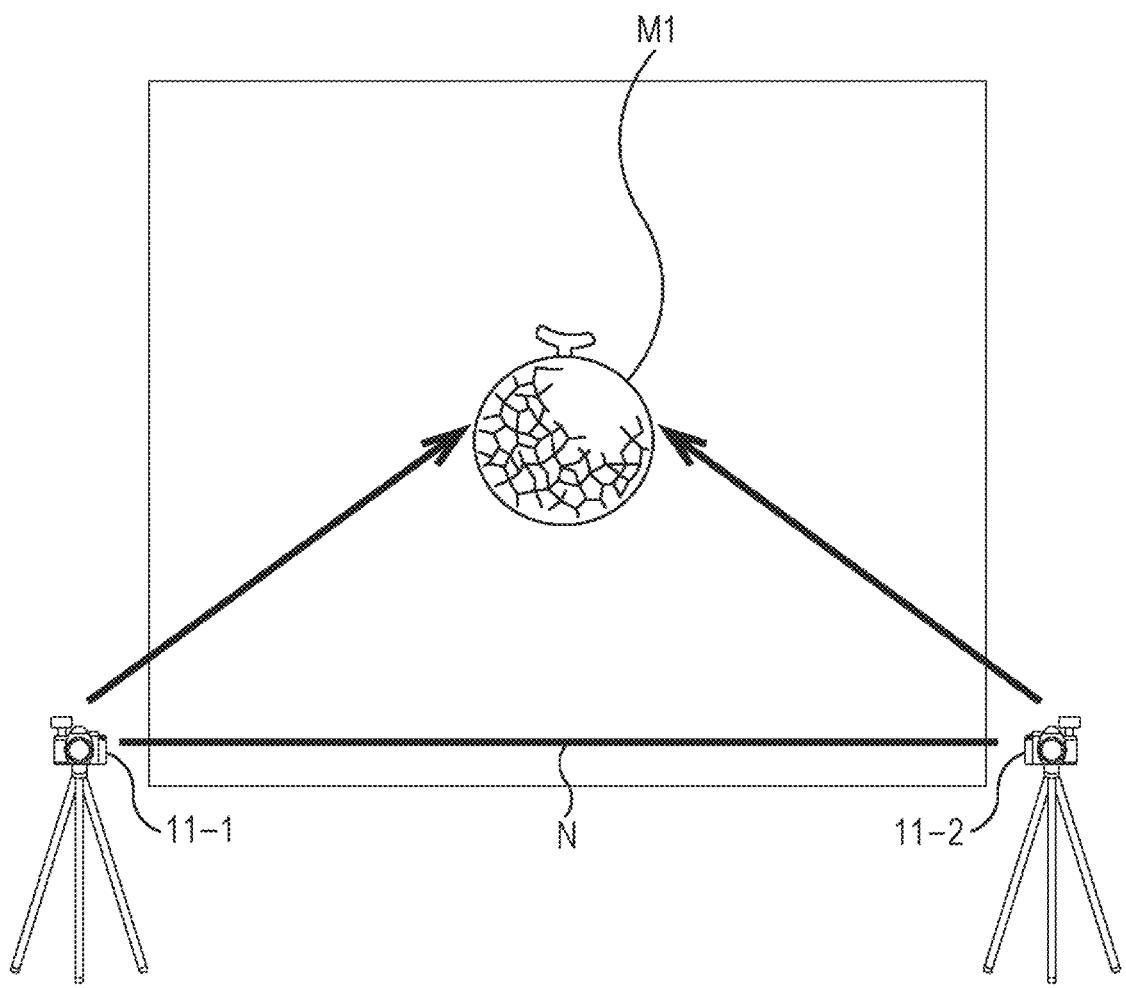
FIG. 13 is an illustrative diagram for describing an imaging principle of a stereoscopic image according to various embodiments of the presently disclosed technology.

In Step S66, the control unit 81 controls the stereoscopic image growth index computation unit 86 such that a stereoscopic image growth index is computed based on a stereoscopic image. As one illustrative specific example, the stereoscopic image growth index computation unit 86 extracts two RGB images included in the growth situation information from at least two sensor cameras 11 which capture RGB images to constitute the stereoscopic image. In other words, as illustrated in FIG. 13, the sensor cameras 11-1 and 11-2 image the same agricultural produce M1 from different angles, and the stereoscopic image growth index computation unit 86 generates a stereoscopic image, i.e., a parallax image from two RGB images captured by the two sensor cameras 11-1 and 11-2. Furthermore, the stereoscopic image growth index computation unit 86 generates a three-dimensional image of agricultural produce present in the target region based on the parallax image, and computes a stereoscopic image growth index from the size. Note that the target region in the processes of Steps S65 and S66 may be a region other than a region obtained based on the RGB images as long as a region of produce that is a target can be specified therefrom, or a region, which, for example, belongs to any of a region of the NDVI image having a high probability of a target present therein and having an NDVI value higher than a predetermined value and a region obtained based on the RGB images, may be set to be the target region.

In Step S67, the control unit 81 controls the growth index computation unit 89 such that a growth index of the target agricultural produce is computed based on the RGB image growth index, the NDVI image growth index, and the stereoscopic image growth index. As one illustrative specific example, the growth index computation unit 89 may assume the average of the three kinds of growth indexes as a growth index, may assume the weighted sum of the indexes as a growth index, or may select one of the indexes as a growth index. In addition, when it is not possible to compute all of the RGB image growth index, the NDVI image growth index, and the stereoscopic image growth index, the average value or weighted sum of computable growth indexes may be set as a growth index.

In Step S68, the control unit 81 searches for management information among the management information accumulated in the management information accumulation unit 88, which corresponds to the IP address included in the growth situation information transmitted from the sensor cameras 11, and updates the growth index included in the searched management information to a value computed from the above-described process.

In Step S69, the control unit 81 controls the harvest time computation unit 87 such that a harvest time is computed based on the growth index, environment information, and growth situation information and information of harvest times of the past. In other words, the harvest time computation unit 87 computes a harvest time of this season anticipated from information of a change in a growth evaluation index of this season based on the relationship between information of a change in growth evaluation indexes and information of harvest times of the past as an anticipated proper harvest time.

In Step S70, the control unit 81 searches for management information among the management information accumulated in the management information accumulation unit 88, which corresponds to the IP address included in the growth situation information transmitted from the sensor cameras 11, and updates information of the anticipated proper harvest time included in the searched management information to a value computed from the above-described process.

In Step S71, the control unit 81 controls the sensor camera operation situation monitoring unit 91 such that whether or not there is an abnormality occurring in the sensor cameras 11 that transmit the growth situation information based on the RGB images is determined. As one illustrative specific example, the sensor camera operation situation monitoring unit 91 compares a current RGB image to an RGB image captured at the previous timing both having the same IP address included in the transmitted growth situation information among the growth situation information accumulated in the growth situation information accumulation unit 82, and determines whether or not there is an abnormality occurring in the sensor cameras 11 based on whether or not a change between the images is greater than a predetermined value. In other words, the sensor cameras 11 are basically fixed-point cameras, and there will not be a significant change in the RGB images even if a predetermined time of an imaging interval is, for example, about one day. Thus, if there is a significant change, it is considered that a problem has arisen in the sensor cameras 11. Therefore, when the sensor camera operation situation monitoring unit 91 compares the currently transmitted RGB image to the previous RGB image, and regards that there is an abnormality occurring in the cameras due to a significant change between the images, the process proceeds to Step S72. Note that the occurrence of an abnormality in the sensor cameras 11 can also be determined from a comparison of NIR images, NDVI images, NDVI average values, variances, high-order variances, and growth indexes.

In Step S72, the sensor camera operation situation monitoring unit 91 regards that there is an abnormality occurring in the sensor cameras 11 that transmit the growth situation information, searches for management information based on the IP address of the sensor cameras 11, and notifies a terminal device 12 managed and operated by the owner of the agricultural produce (farmland) included in the searched management information or a mobile telephone not shown in the drawings of the occurrence.

On the other hand, when it is regarded that no abnormality occurs in Step S71, the process of Step S72 is skipped.

In Step S73, the control unit 81 determines whether or not the growth index is higher than a predetermined threshold value, and the anticipated proper harvest time is coming. In Step S73, when, for example, the growth index is higher than the predetermined threshold value and the anticipated proper harvest time is coming, in other words, when it is regarded that the very day corresponding to the anticipated proper harvest time or a day a predetermined number of days earlier than the very day is coming, the process proceeds to Step S74.

In Step S74, the control unit 81 controls the harvest plan creation unit 93 such that a harvest plan is created. For example, the harvest plan creation unit 93 estimates an amount of crops to harvest from a range in which anticipated proper harvest times overlap in management information managed according to IP addresses, and makes a harvest schedule of how to proceed with the harvesting process from a harvest start day based on processing performance of agricultural machines for harvesting which may be registered in advance by the owner of the same agricultural produce (farmland).

In Step S75, the control unit 81 controls the communication unit 92 such that the information of the harvest plan created by the harvest plan creation unit 93 is transmitted to the terminal device 12 managed and operated by the farmer. Note that the information of the harvest plan may also be transmitted to the terminal devices 12 managed and operated by the distributor, the retailer, and the consumer. With this operation, the distributor, the retailer, and the consumer can make their own distribution plan, sales plan, and purchase plan from the information of the harvest plan.

After this process, in Step S91 (of FIG. 12), the control unit 61 of each terminal device 12 controls the communication unit 64 such that whether or not the harvest plan has been transmitted is determined, and the same process is repeated until the plan is transmitted. When the harvest plan is transmitted through, for example, the process of Step S75 of FIG. 12, in Step S91, the process proceeds to Step S92.

In Step S92, the control unit 61 controls the communication unit 64 such that the transmitted information of the harvest plan is received.

In Step S93, the control unit 61 causes the information of the harvest plan received by the communication unit 64 to be displayed on the display unit 66.

In Step S76 (of FIG. 11), the control unit 81 controls the delivery plan creation unit 94 such that a delivery plan is created. For example, the delivery plan creation unit 94 estimates an amount of crops to harvest from a range in which anticipated proper harvest times overlap in management information managed according to IP addresses, and makes a delivery schedule of how to proceed with the delivery process from the harvest start day based on transportation performance of delivery vehicles for delivery which may be registered in advance by the contract distributor.

In Step S77, the control unit 81 controls the communication unit 92 such that the information of the delivery plan generated by the delivery plan creation unit 94 is transmitted to the terminal device 12 managed and operated by the contract distributor. Note that since a process performed in the terminal device 12 is merely reception and display of the delivery plan instead of the harvest plan in the process described with reference to the flowchart of FIG. 12, description of the process is omitted. In addition, in the processes of Steps S76 and S77, a delivery plan, a sales plan, and a purchase plan of all farmlands including farmlands on which contracts are not made with the distributor, the retailer, and the consumer may be transmitted to the distributor, the retailer, and the consumer who are shown in FIG. 1 as contractors of a series of services. Furthermore, in the processes of Steps S76 and S77, a delivery plan, a sales plan, and a purchase plan for farmlands within regions that are within business scopes of the distributor, the retailer, and the consumer may be transmitted to the distributor, the retailer, and the consumer who are shown in FIG. 1 as contractors of a series of services. In such an illustrative case, for a big distribution company, for example, the delivery plan may be transmitted to branches thereof.

In Step S78, the control unit 81 controls the sales plan creation unit 95 such that a sales plan is created. As one illustrative specific example, the sales plan creation unit 95 estimates an amount of crops to harvest from a range in which anticipated proper harvest times overlap in management information managed according to IP addresses, and makes a sales schedule of how to proceed sales from the harvest start day based on an amount of produce displayable in a store front which is registered in advance by the contract retailer.

In Step S79, the control unit 81 controls the communication unit 92 such that information of the sales plan created by the sales plan creation unit 95 is transmitted to the terminal device 12 managed and operated by the contract retailer. Note that since a process performed in the terminal device 12 is merely reception and display of the sales plan instead of the harvest plan in the process described with reference to the flowchart of FIG. 12, description thereof is omitted. In addition, in the processes of Steps S78 and S79, it may be configured that a retailer located near a farmland is selected from retailers shown in FIG. 1 serving as contractors of a series of services for each farmland, and the sales plan is transmitted to the selected retailer. In such an illustrative case, for example, the sales plan may be transmitted to branches of a big retailer such as a supermarket, and further, information to which a delivery plan is added may be transmitted thereto.

In Step S80, the control unit 81 controls the purchase plan creation unit 96 such that a purchase plan is created. As one illustrative specific example, the purchase plan creation unit 96 estimates an amount of crops to harvest from a range in which anticipated proper harvest times overlap in management information managed according to IP addresses, and makes a purchase schedule of how to proceed purchase from the harvest start day based on a desired amount of produce to purchase which is registered in advance by the contract consumer.

In Step S81, the control unit 81 controls the communication unit 92 such that information of the purchase plan generated by the purchase plan creation unit 96 is transmitted to the terminal device 12, and the process returns to Step S61. Note that since a process performed in the terminal device 12 is merely reception and display of the purchase plan instead of the harvest plan in the process described with reference to the flowchart of FIG. 12, description thereof is omitted. In addition, in the processes of Steps S80 and S81, the purchase plan for a farmland of produce to be purchased may be transmitted to each consumer out of consumers shown in FIG. 1 that are contractors of a series of services. In addition, the purchase plan may be generated in accordance with a sales plan of a specific retailer, for example, who is located near the location of a consumer and transmitted the plan to the consumers who purchase the produce from the retailer.

In addition, in Step S73, when the growth index is not higher than the predetermined threshold value, the process proceeds to Steps S83 to S86. Note that since the processes of Steps S83 to S86 are the same as the processes of Steps S74 S76, S78, and S80, description thereof is omitted. In other words, even when the growth index is not higher than the predetermined threshold value in Step S73, it may be configured that the harvest plan, the delivery plan, the sales plan, and the purchase plan are created, and when there is an inquiry with regard to each of the plans, a response may be made to each of the plans, and developments of the growth index may be transmitted whenever the developments take place.

In other words, from the above process, pieces of the growth situation information that are transmitted from the sensor cameras 11 at a predetermined time interval are sequentially accumulated. During that time, the growth index and the anticipated proper harvest time in the management information managed based on the IP addresses of the sensor cameras 11 are sequentially updated and recorded based on pieces of the growth situation information. As a result, the growth index, and the anticipated proper harvest time are updated to the latest information at a predetermined time interval, and when the anticipated proper harvest time is coming, the updated information can be transferred to the terminal devices 12 managed and operated by each of the farmer, the contract distributor, the contract retailer, and the contract consumer in real-time as information of the harvest plan, the delivery plan, the sales plan, and the purchase plan. In addition, since proper behaviors can be taken in accordance with the anticipated proper harvest time by transferring the information of the harvest plan, the delivery plan, the sales plan, and the purchase plan, efficient harvest, delivery, sales, and purchase are possible. Furthermore, by comparing the RGB images in a time series manner thereby detecting an abnormality in the sensor cameras 11, whether or not the sensor cameras 11 are appropriately installed can be monitored. In addition, since the sensor cameras 11 can be used as a communication path even when a sensor camera 11 is stolen or moved to another position due to a storm, or when crops are stolen, an abnormality can be detected by comparing transmitted positional information to the positional information included in the management information. In addition, when the sensor cameras 11 can be used as a communication path even when an imaging direction or angle of the sensor cameras 11 is changed due to any cause, an abnormality can be assumed to occur and detected through the same process. Note that the harvest plan, the delivery plan, the sales plan, and the purchase plan may be transferred on the very day specified as the anticipated proper harvest time, or a day a predetermined number of days earlier from the specified day.

[Inquiry Response Process]

Figure 14:
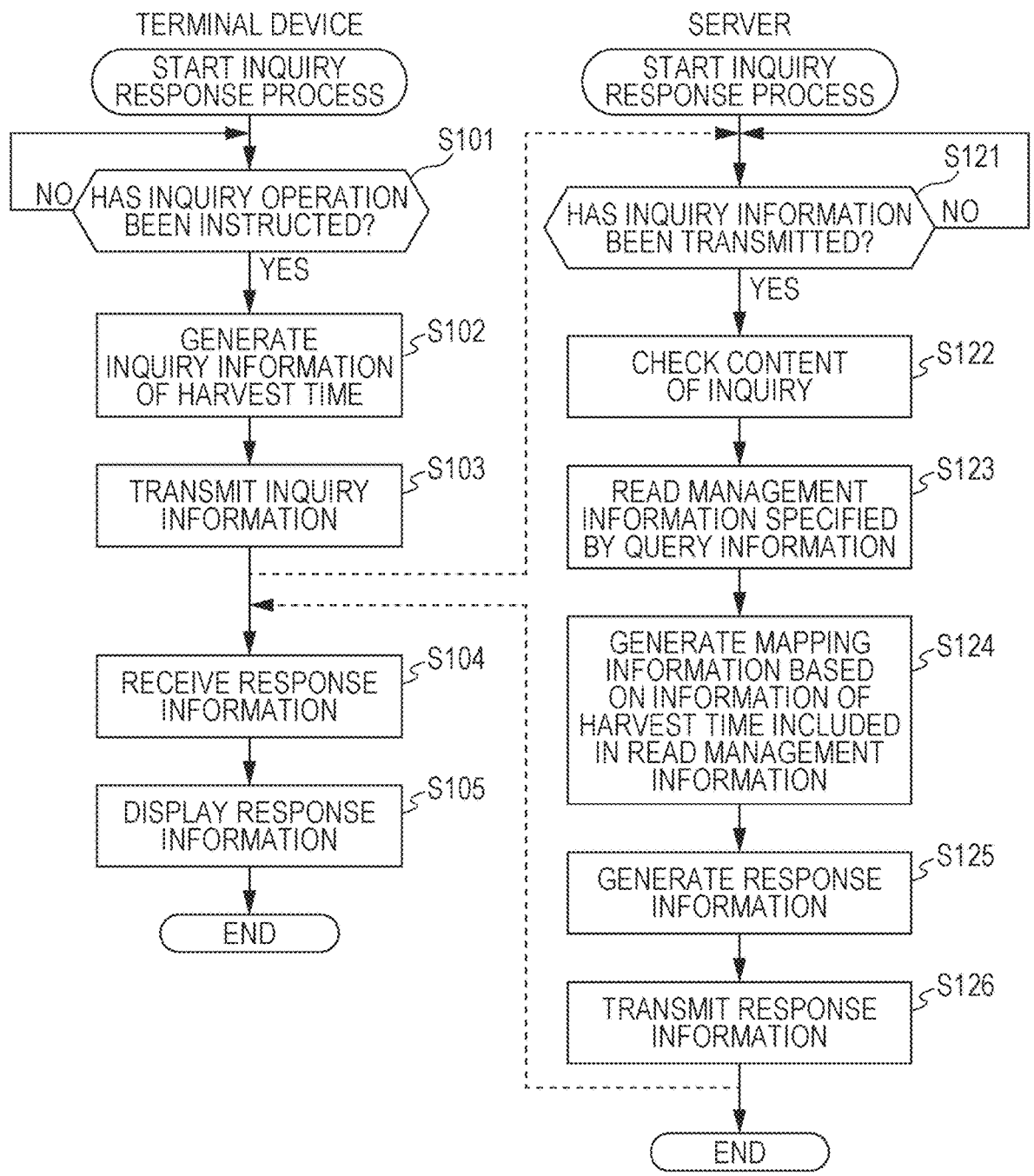
FIG. 14 is an illustrative flowchart for describing an inquiry response process between the terminal device and the server according to various embodiments of the presently disclosed technology.

Regarding FIG. 14, an inquiry response process will be described. Note that, here, processes of transmitting inquiry information for making an inquiry of a harvest time to the server 14 by the terminal device 12 managed and operated by the farmer, and receiving and displaying the response information will be described. Note that, since the same process is performed when the contract retailer, the contract consumer, and the contract distributor make the same inquiry, description thereof is omitted.

In other words, in Step S101, the control unit 61 of the terminal device 12 controls the operation unit 63 such that whether or not an inquiry operation is made according to an operation by a user is determined, and the same process is repeated until it is regarded that there is an inquiry operation. When it is regarded that there is an inquiry operation in Step S101, the process proceeds to Step S102.

In Step S102, the inquiring unit 62 generates the inquiry information for making an inquiry of a harvest time associated with the IP address for identifying the sensor cameras 11 monitoring crops cultivated in the farmland of the contract farmer stored in the IP address storage unit 65. Note that, when the contract distributor, retailer, and consumer shown in FIG. 1 who receive a series of services conclude a contract for a service, not for each farmland (each IP address), the inquiring unit 62 stores a relationship table in advance in which business scopes of the distributor, the retailer, and the consumer are associated with the IP addresses corresponding to the sensor cameras 11, and generates inquiry information including the IP addresses according to the business scopes of the distributor, the retailer, and the consumer.

In Step S103, the control unit 61 controls the communication unit 64 such that the inquiry information generated by the inquiring unit 62 to make an inquiry of the harvest time is transmitted to the server 14 via the network 13.

In Step S121, the control unit 81 of the server 14 controls the inquiry reception unit 97 such that whether or not the inquiry information has been transmitted from the communication unit 92 is determined, and the same process is repeated until the information is transmitted. In addition, when it is regarded that the inquiry information is transmitted in Step S121, the process proceeds to Step S122.

In Step S122, the control unit 81 controls the inquiry reception unit 97 such that the inquiry information transmitted from the communication unit 92 is acquired, and the content of the inquiry is checked.

In Step S123, the control unit 81 searches for the management information accumulated in the management information accumulation unit 88 based on the IP address included in the inquiry information, and reads information of an anticipated proper harvest time and information of regions in the searched management information. Here, when there are a plurality of sensor cameras 11 monitoring crops cultivated by the farmer, a plurality of IP addresses are included. In addition, here, the searched information of the anticipated proper harvest time is based not only on a sensor camera 11 installed in the farmer's own farmland, but also on an IP address specifying a sensor camera 11 designated by a user.

In Step S124, the control unit 81 controls the mapping unit 90 such that the information of the anticipated proper harvest time is mapped in positions corresponding to the read information of the regions according to a schedule, and thereby anticipated proper harvest time mapping information is generated.

In Step S125, the control unit 81 controls the response creation unit 98 such that response information that includes the generated anticipated proper harvest time mapping information is created.

In Step S126, the control unit 81 controls the communication unit 92 such that the response information that includes the created anticipated proper harvest time mapping information is transmitted to the terminal device 12 that transmitted the inquiry information.

In Step S104, the control unit 61 of the terminal device 12 controls the communication unit 64 such that the response information is received.

In Step S105, the control unit 61 of the terminal device 12 causes the response information that includes the received anticipated proper harvest time mapping information to be displayed on the display unit 66.

From the processes described above, the information of the anticipated proper harvest time can acquire the mapped information. In addition, with the displayed mapping information, the information of the anticipated proper harvest time can be transferred in real-time on-demand. Note that, in the above, the inquiry response process performed by the terminal device 12 managed by the farmer has been described, but the same process can also be performed in the terminal devices 12 managed by the contract distributor, the contract retailer, and the contract consumer. In addition, in the above, the content of the inquiry is the information of the anticipated proper harvest time, but even if the content is other information, for example, the harvest plan, the delivery plan, the sales plan, and the purchase plan managed by the server 14, an inquiry may be made through the same process, or a response may be made to the inquiry. Furthermore, it is possible that, for example, mapping information of anticipated proper harvest times of crops is transmitted to the terminal devices 12 managed by the farmer, the distributor, and the consumer, or retailers are classified for each agricultural produce and mapping information of anticipated proper harvest times is transmitted to the retailers. In other words, the information of the anticipated proper harvest times, for example, the name of agricultural produce, the time to harvest, and the name of a branch to be delivered to can be transmitted to a big supermarket.

Note that, in the above, the example in which RGB images and an NIR image are captured by the sensor cameras 11, growth situation information including the images is transmitted to the server 14, an RGB image growth index and an NDVI image growth index that are computed by the server 14, and an anticipated proper harvest time that is computed have been described. However, by providing the same function of the server 14 in the sensor cameras 11, it may be configured that, by the sensor cameras 11, a region in which target agricultural produce is imaged is specified, an RGB image growth index and an NDVI image growth index of a region specified as the region of the RGB images and the NDVI image in which the agricultural produce is imaged are computed, growth situation information including the indexes are generated, and the information is supplied to the server 14. In addition, in addition to these functions, the sensor cameras 11 may capture a stereoscopic image in cooperation with another sensor camera 11 nearby, and compute a stereoscopic image growth index. Furthermore, the sensor cameras 11 may compute a growth index and an anticipated proper harvest time based on the RGB image growth index, the NDVI image growth index, and the stereoscopic image growth index obtained as above. In this illustrative case, when the anticipated proper harvest time is computed, the sensor cameras 11 may read growth situation information of the past accumulated in the server 14, and compute the anticipated proper harvest time also using the growth situation information of the past.

In addition, in the above, the configuration example in which the sensor cameras 11, the terminal devices 12, and the server 14 are included has been described for the configuration of the information processing system, however, a cloud computer may be used instead of the server 14.

2. First Modification Example

Figure 15:
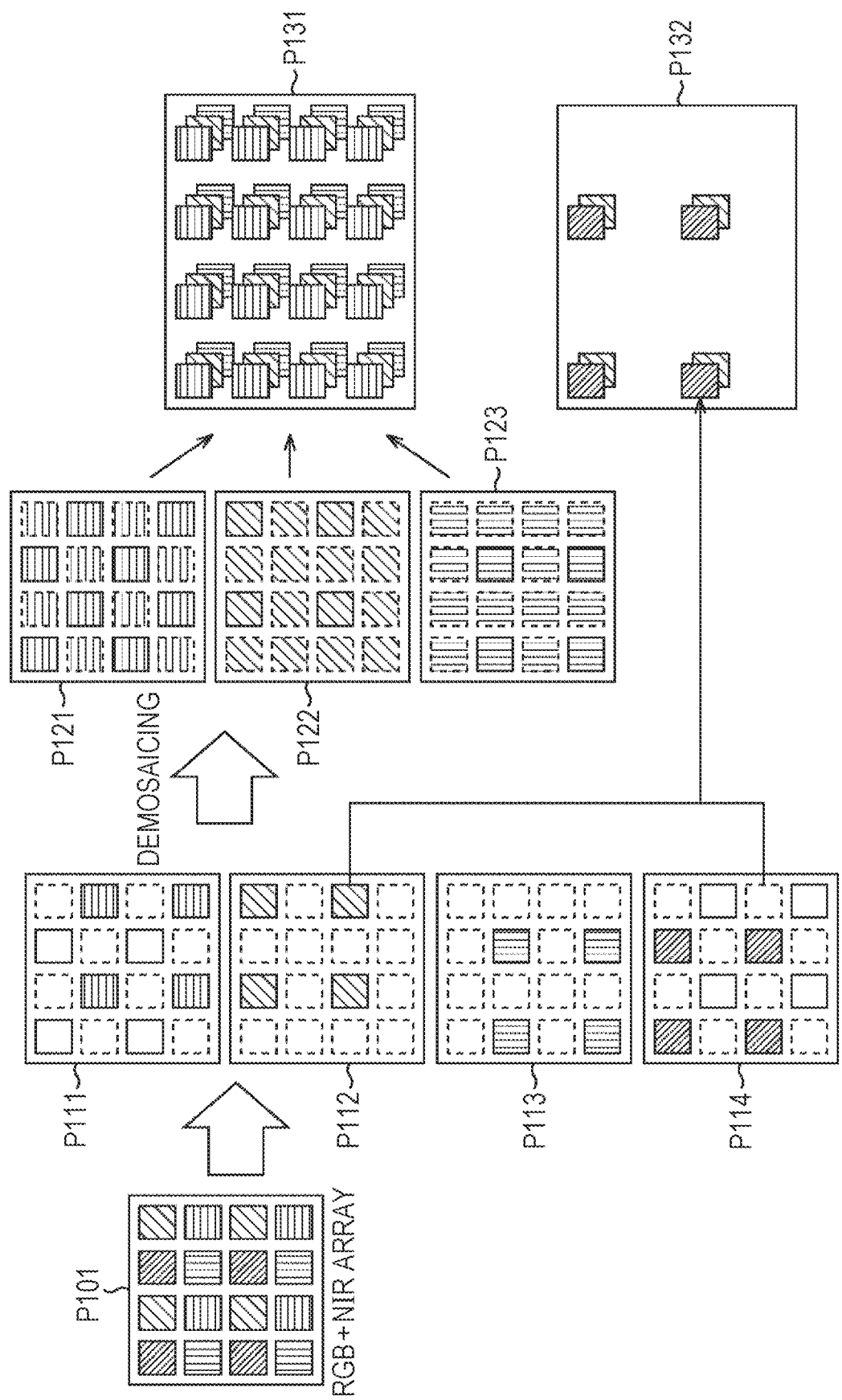
FIG. 15 is an illustrative diagram for describing a first modification example of the sensor according to various embodiments of the presently disclosed technology.

In the above, the example in which information captured by the sensor cameras 11 is demosaiced to generate RGB and NIR component signal images has been described, however, as illustrated in FIG. 15, for example, using images P112 and P114 that include red light signals and NIR signals before being demosaiced, an NDVI image P132 as shown by an image P132 may be generated. Since the demosaicing process can be omitted, or the number of pixels to be dealt with can be reduced with this operation, a processing load can be lowered and a processing speed can improve. Note that, since the images P111, P113, P121 to P123, and P131 are the same as the images P11, P13, P21 to P23, and P31 of FIG. 3, description thereof will be omitted.

3. Second Modification Example

Figure 16:
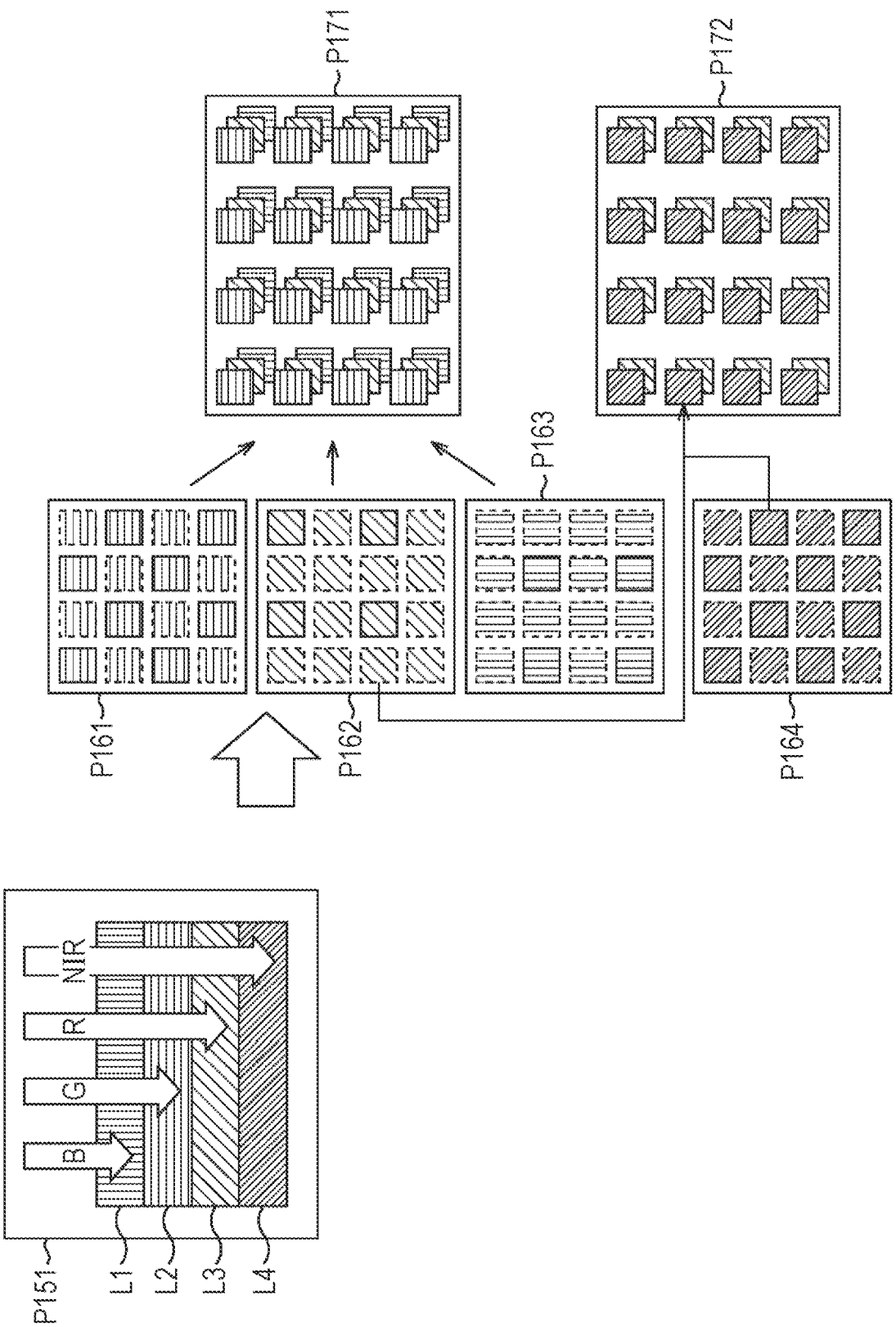
FIG. 16 is an illustrative diagram for describing a second modification example of the sensor according to various embodiments of the presently disclosed technology.

In addition, in the above, the example in which pixels of the RGB and NIR component signals are arrayed in a direction of a plane of the sensor cameras 11 has been described, however, as illustrated in FIG. 16, for example, the sensor 31 may be configured by laminating sensor layers perpendicular to a light traveling direction so as to generate component signal images. In other words, in FIG. 16, a blue light sensor layer L1, a green light sensor layer L2, a red light sensor layer L3, and an NIR sensor layer L4 are configured to be laminated from above the drawing as shown by an image P151. Each layer has a sensor structure in which only a color component with a target wavelength is detected. As a result, images P161 to P163 that include green light, red light, blue light, and NIR component signal images of the images P161 to P164 of each layer are generated. As a result, an RGB image P171 is generated from the images P161 to P163, and an NDVI image P172 is generated from the images P162 and P164.

4. Third Modification Example

Figure 17:
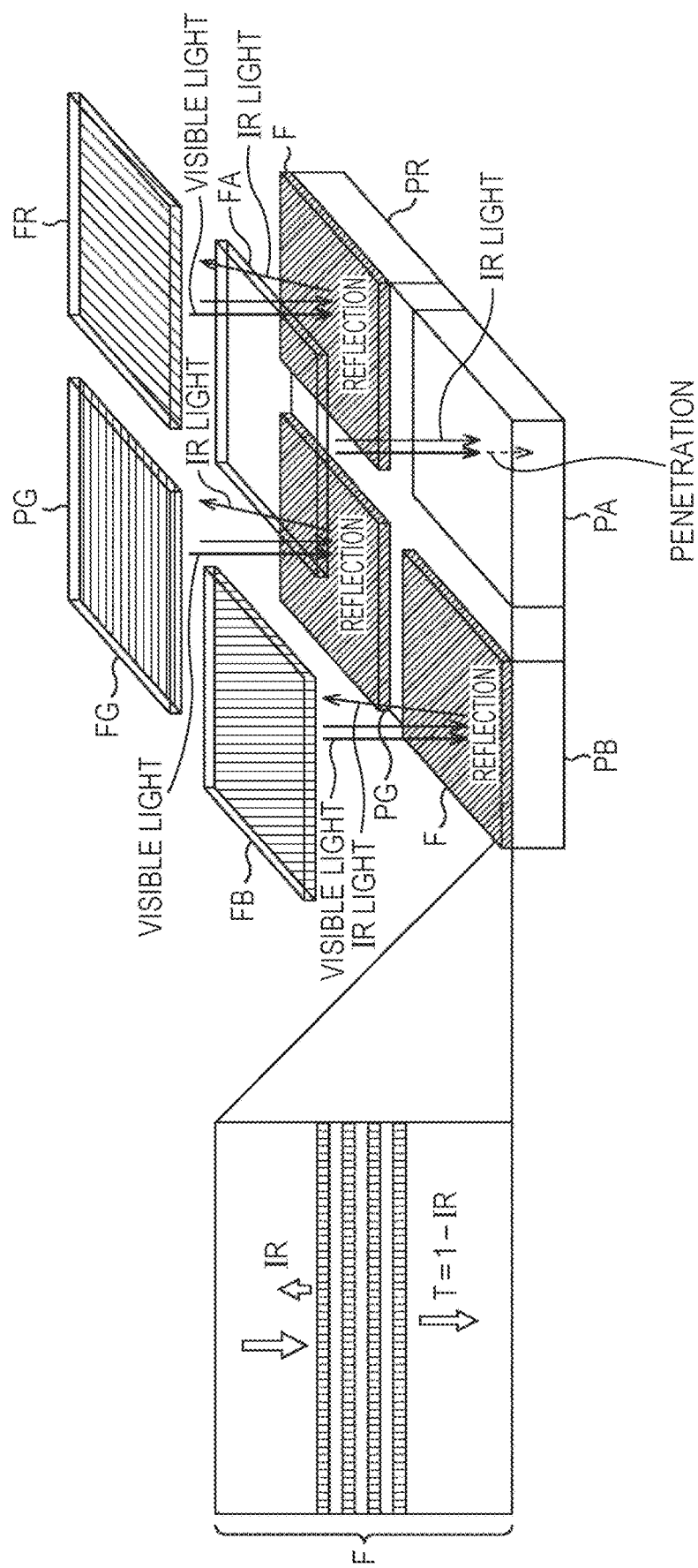
FIG. 17 is an illustrative diagram for describing a third modification example of the sensor according to various embodiments of the presently disclosed technology.

Furthermore, with regard to the sensor 31 that detects RGB component signals, it may be configured that, for example, an IR cut filter F that includes a dielectric laminated film, for example, a laminated film made of SiO or SiN as illustrated in the left part of FIG. 17 is provided under RGB color filters FR, FG, and FB as illustrated in the right part of FIG. 17, so that the sensor that detects RGB signal components does not detect NIR, and the IR cut filter F is not provided only under a black (visible light cut) filter FA of an NIR sensor. Note that the right part of FIG. 17 is a perspective appearance diagram of two pixels x two pixels of the sensor 31, and the left part of the drawing is an enlarged cross-sectional diagram of the IR cut filter F, which shows that infrared light IR is blocked by the IR cut filter and only light T other than the infrared light IR transmits the sensor. Note that the black filter FA may be configured not to include a color filter.

5. Fourth Modification Example

Figure 18:
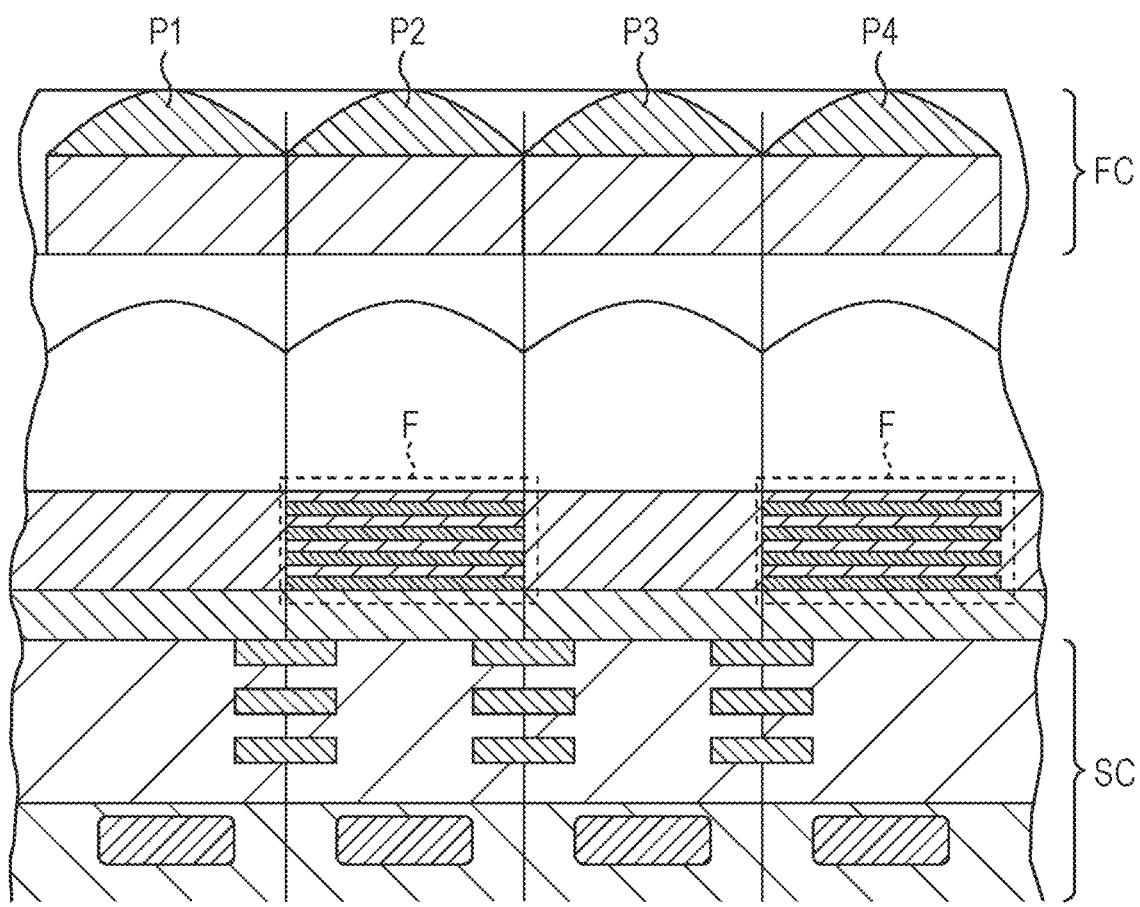
FIG. 18 is an illustrative diagram for describing a fourth modification example of the sensor according to various embodiments of the presently disclosed technology.

In addition, the sensor 31 that detects NIR component signals may be configured such that the IR cut filters F are provided under RGB color filters FC and above sensors SC as illustrated in, for example, FIG. 18 so that a sensor that detects RGB signal components does not detect NIR, and the IR cut filters F are not provided only above NIR sensors SC. Note that FIG. 18 is a cross-sectional diagram for four pixels of the sensor 31, showing a configuration of a pixel P1 for NIR, a pixel P2 for light other than NIR, a pixel P3 for NIR, and a pixel P4 for light other than NIR arranged from the left of the drawing.

Note that, in the above, the example in which an NDVI image is generated based on RGB signal components and NIR signal components and an NDVI image growth index obtained from the generated NDVI image is used has been described, however, other growth indexes may be used as long as the growth indexes are obtained based on the RGB signal components and NIR signal components. Thus, it may be configured that, instead of the NDVI image, for example, a Simple Ratio (SR) image, a Global Environment Monitoring Index (GEMI) image, a Soil Adjusted Vegetation Index (SAVI) image, an Enhanced Vegetation Index (EVI) image, a Perpendicular Vegetation Index (PVI) image, a Photochemical Reflectance Index (PRI) image, a Structure Insensitive Pigment Index (SIPI) image, a Plant Sensing Reflectance Index (PSRI) image, a Chlorophyll Index (CI) image, a Modified Simple Ratio (mSR) image, a Modified Normalized Difference (mND) image, a Canopy Chlorophyll Index (CCI) image, a Water Index (WI) image, a Normalized Difference Water Index (NDWI) image, a Cellulose Absorption Index (CAI) image, a Ratio Vegetation Index (RVI) image, a Kind of Vegetation Index (KVI) image, and a Difference Vegetation Index (DVI) image, which are obtained based on RGB signal components and NIR signal components, are used and growth indexes corresponding to the images are computed and used. Furthermore, by combining a plurality of kinds of images obtained based on RGB signal components and NIR signal components, an image growth index of the combined image may be obtained and used.

The series of processes described above can be executed by hardware or by software. When the series of processes is executed by software, a program constituting the software is installed in a computer incorporated into dedicated hardware, or in, for example, a general-purpose personal computer that can execute various functions by installing various programs therein from a recording medium.

Figure 19:
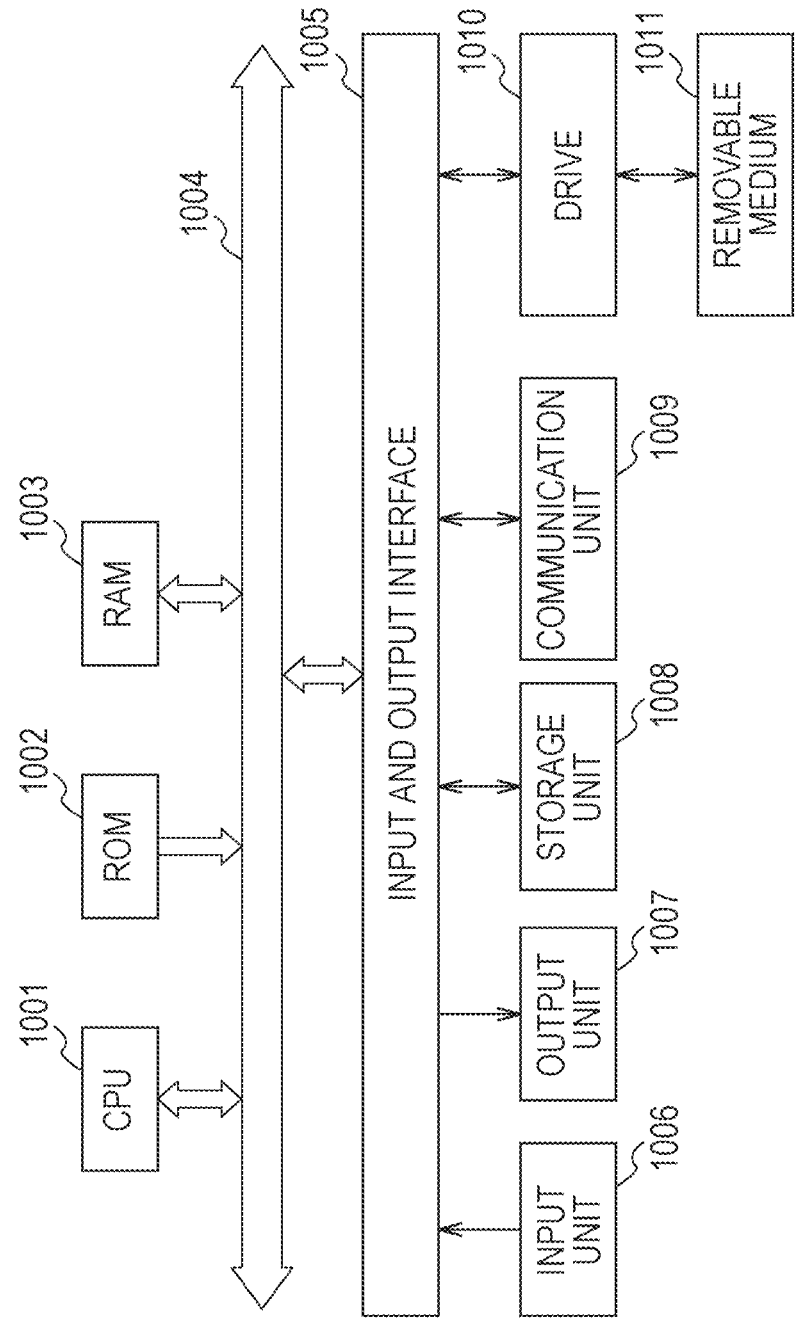
FIG. 19 is an illustrative diagram for describing a configuration example of a general-purpose personal computer according to various embodiments of the presently disclosed technology.

FIG. 19 illustrates an illustrative configuration example of a general-purpose personal computer. The personal computer has a Central Processing Unit (CPU) 1001 built therein. The CPU 1001 is connected to an input and output interface 1005 via a bus 1004. A Read Only Memory (ROM) 1002 and a Random Access Memory (RAM) 1003 are connected to the bus 1004.

An input unit 1006 that is configured by an input device such as a keyboard or a mouse by which a user inputs operation commands, an output unit 1007 that outputs process operation screens or process result images on a display device, a storage unit 1008 that is configured by a hard disk drive in which programs and various kinds of data are stored, and a communication unit 1009 that is configured by a Local Area Network (LAN) adaptor and executes communication processes via a network represented by the Internet are connected to the input and output interface 1005. In addition, a drive 1010 that reads and writes data from and to a removable medium 1011 such as a magnetic disk (including a flexible disk), an optical disc (including a Compact Disc-Read Only Memory (CD-ROM) or a Digital Versatile Disc (DVD)), a magneto-optical disc (including a Mini Disc (MD)), or a semiconductor memory is connected thereto.

The CPU 1001 executes various processes according to programs stored in the ROM 1002 or programs read from the removable medium 1011 such as a magnetic disk, an optical disc, a magneto-optical disc, or a semiconductor memory and installed in the storage unit 1008 and loaded on the RAM 1003 from the storage unit 1008. The RAM 1003 also appropriately stores data for the CPU 1001 to execute various processes. Such data may be necessary for the CPU 1001 to execute various processes.

A computer configured as described above performs the series of processes described above when the CPU 1001 causes, for example, programs stored in the storage unit 1008 to be loaded on the RAM 1003 and executes the programs via the input and output interface 1005 and the bus 1004.

The programs executed by the computer (the CPU 1001) can be provided by being recorded on the removable medium 1011, for example, a package medium. In addition, the programs can be provided via a wired or a wireless transmission medium such as a local area network, or the Internet, or in the form of digital satellite broadcasting.

The programs can be installed in the storage unit 1008 in the computer via the input and output interface 1005 by loading the removable medium 1011 in the drive 1010. In addition, the programs can be installed in the storage unit 1008 by being received by the communication unit 1009 via a wired or a wireless transmission medium. In addition, the programs can be installed in the ROM 1002 or the storage unit 1008 in advance.

Note that the programs executed by the computer may be programs by which the processes are performed in a time-series manner in the order as described herein, or may be a program by which the processes are performed, for example, in parallel or at timings such as when there is a call-out.

In addition, in the present specification, a system means a set of a plurality of constituent elements (such as devices or modules (components)), and it does not matter that all of the constituent elements are accommodated in the same housing. Therefore, a plurality of devices which are accommodated in individual housings and connected to one another via a network and one device of which a plurality of modules are accommodated in one housing falls into a system.

Note that embodiments of the presently disclosed technology are not limited to the embodiments described above, and can be variously modified in the scope not departing from the gist of the presently disclosed technology.

For example, the presently disclosed technology can adopt the cloud computing configuration in which one function is divided and shared by a plurality of devices via a network.

In addition, execution of each step described in the flowcharts above can be done by one device or dividedly by a plurality of devices.

Further, when a plurality of processes are included in one step, execution of the plurality of processes included in the step can be done by one device or dividedly by a plurality of devices.

Note that the presently disclosed technology can also adopt the following configurations.

(A-1) A method comprising: obtaining image information of an organism comprising a set of optical data; calculating a growth index based on the set of optical data; and calculating an anticipated harvest time based on the growth index, wherein the image information comprises at least one of: (a) visible image data obtained from an image sensor and non-visible image data obtained from the image sensor, and (b) a set of image data from at least two image capture devices, wherein the at least two image capture devices capture the set of image data from at least two positions.

(A-2) The method of (A-1), further comprising transferring the anticipated harvest time to an outside party.

(A-3) The method of (A-2), wherein the outside party is at least one of a retailer, a general consumer, a restaurant, and a food producer.

(A-4) The method of any one of (A-1)-(A-3), wherein the visible image data is generated based on a demosaiced RGB pixel signal.

(A-5) The method of any one of (A-1)-(A-4), wherein the non-visible image data is generated based on a demosaiced R and IR signal.

(A-6) The method of any one of (A-1)-(A-4), wherein the non-visible image data is generated based on a R and IR signal without demosaicing.

(A-7) The method of any one of (A-1)-(A-3), wherein the visible image data is generated based on a demosaiced RGB pixel signal, and wherein the near-infrared ray image data is generated based on a demosaiced R and IR signal.

(A-8) The method of any one of (A-1)-(A-3), wherein the visible image data is generated based on a demosaiced RGB pixel signal, and wherein the near-infrared ray image data is generated based on a R and IR signal without demosaicing.

(A-9) The method of any one of (A-1)-(A-8), wherein the set of optical data is obtained using a stack type image sensor, wherein the stack type image sensor has a blue light sensor layer stacked on a green light sensor layer, wherein the green light sensor layer is stacked on a red light sensor layer, and wherein the red light sensor layer is stacked on an near-infrared ray (NIR) sensor layer.

(A-10) The method of any one of (A-1)-(A-8), wherein the set of optical data is obtained using an image sensor comprising a set of RGB color filters provided over a laminated film, wherein the laminated film comprises at least one of SiO and SiN, and wherein the set of RGB color filters comprise a FR color filter, a FG color filter, and a FB color filter.

(A-11) The method of any one of (A-1)-(A-8), wherein the set of optical data is obtained using an image sensor comprising a set of RGB color filters provided over a set of infrared (IR) cut filters, wherein the set of IR cut filters is provided over a set of image sensors.

(A-12) The method of any one of (A-1)-(A-11), further comprising calculating a parallax image data based on at least two of the image data from the set of image data obtained from the at least two image capture devices; and calculating the growth index based on the parallax image data, wherein the at least two of the image data are captured from at least one of: two angles and the at least two positions by the at least two image capture devices.

(A-13) A system comprising: an image capture device, wherein at least one of the server and the image capture device is configured to: obtain image information of an organism comprising a set of optical data; calculate a growth index based on the set of optical data; and calculate an anticipated harvest time based on the growth index, wherein the image information comprises at least one of: (a) visible image data obtained from an image sensor and non-visible image data obtained from the image sensor, and (b) a set of image data from at least two image capture devices, wherein the at least two image capture devices capture the set of image data from at least two positions.

(A-14) The system of (A-13), further comprising a server, wherein the image capture device is in communication with the server.

(A-15) The system of (A-14), wherein the at least one of the server and the image capture device is further configured to transfer the anticipated harvest time to an outside party.

(A-16) The system of any one of (A-13)-(A-15), wherein the visible image data is generated based on a demosaiced RGB pixel signal.

(A-17) The system of any one of (A-13)-(A-16), wherein the non-visible image data is generated based on a demosaiced R and IR signal.

(A-18) The system of any one of (A-13)-(A-16), wherein the non-visible image data is generated based on a R and IR signal without demosaicing.

(A-19) The system of any one of (A-13)-(A-18), wherein the set of optical data is obtained using a stack type image sensor, wherein the stack type image sensor has a blue light sensor layer stacked on a green light sensor layer, wherein the green light sensor layer is stacked on a red light sensor layer, and wherein the red light sensor layer is stacked on an near-infrared ray sensor layer.

(A-20) The system of any one of (A-13)-(A-18), wherein the set of optical data is obtained using an image sensor comprising a set of RGB color filters provided over a laminated film, wherein the laminated film comprises at least one of SiO and SiN, and wherein the set of RGB color filters comprise a FR color filter, a FG color filter, and a FB color filter.

(A-21) The system of any one of (A-13)-(A-18), wherein the set of optical data is obtained using an image sensor comprising a set of RGB color filters provided over a set of infrared (IR) cut filters, wherein the set of IR cut filters is provided over a set of image sensors.

(A-22) The system of any one of (A-13)-(A-21), wherein the at least one of the server and the image capture device is further configured to: calculate a parallax image data based on at least two of the image data from the set of image data obtained from the at least two image capture devices;

and calculate the growth index based on the parallax image data, wherein the at least two of the image data are captured from at least one of: two angles and the at least two positions by the at least two image capture devices.

(A-23) A tangible, non-transitory computer-readable medium having stored thereon instructions that cause a processor to execute a method, the method comprising: obtaining image information of an organism comprising a set of optical data; calculating a growth index based on the set of optical data; and calculating an anticipated harvest time based on the growth index, wherein the image information comprises at least one of: (a) visible image data obtained from an image sensor and non-visible image data obtained from the image sensor, and (b) a set of image data from at least two image capture devices, wherein the at least two image capture devices capture the set of image data from at least two positions.

(A-24) The computer-readable medium of (A-23), wherein the method further comprises transferring the anticipated harvest time to an outside party.

(A-25) The computer-readable medium of (A-24), wherein the outside party is at least one of a retailer, a general consumer, a restaurant, and a food producer.

(A-26) The computer-readable medium of any one of (A-23)-(A-25), wherein the visible image data is generated based on a demosaiced RGB pixel signal.

(A-27) The computer-readable medium of any one of (A-23)-(A-26), wherein the non-visible image data is generated based on a demosaiced R and IR signal.

(A-28) The computer-readable medium of any one of (A-23)-(A-27), wherein the method further comprises calculating a parallax image data based on at least two of the image data from the set of image data obtained from the at least two image capture devices; and calculating the growth index based on the parallax image data, wherein the at least two of the image data are captured from at least one of: two angles and the at least two positions by the at least two image capture devices.

Moreover, note that the presently disclosed technology can also adopt the following configurations.

(B-1) An information processing system which includes an imaging unit that captures an image of agricultural produce as an RGB image and a near-infrared ray (NIR) image, a specification unit that specifies a region of the image in which a subject that is the agricultural produce is imaged, and a growth index computation unit that computes a growth index of the agricultural produce based on a growth index image obtained from the RGB image, the NIR image, and a red image of the RGB image of the region in the image which is specified by the specification unit and in which the subject is imaged.

(B-2) The information processing system described in (B-1) above, in which the growth index image is any one of or a combination of a Normalized Difference Vegetation Index (NDVI) image, a Simple Ratio (SR) image, a Global Environment Monitoring Index (GEMI) image, a Soil Adjusted Vegetation Index (SAVI) image, an Enhanced Vegetation Index (EVI) image, a Perpendicular Vegetation Index (PVI) image, a Photochemical Reflectance Index (PRI) image, a Structure Insensitive Pigment Index (SIPI) image, a Plant Sensing Reflectance Index (PSRI) image, a Chlorophyll Index (CI) image, a Modified Simple Ratio (mSR) image, a Modified Normalized Difference (mND) image, a Canopy Chlorophyll Index (CCI) image, a Water Index (WI) image, a Normalized Difference Water Index (NDWI) image, a Cellulose Absorption Index (CAI) image, a Ratio Vegetation Index (RVI) image, a Kind of Vegetation Index (KVI) image, and a Difference Vegetation Index (DVI) image.

(B-3) The information processing system described in (B-1) above, in which the imaging unit is configured to include image sensors of each color of the RGB image and an image sensor for NIR.

(B-4) The information processing system described in (B-3) above, in which the imaging unit has a planar array of pixels having colors for the RGB image and NIR.

(B-5) The information processing system described in (B-3) above, in which the imaging unit has pixels having colors for the RGB image and NIR which are arrayed so as to be laminated in a light traveling direction.

(B-6) The information processing system described in (B-1) above, which further includes a growth index image computation unit that computes the growth index image of the agricultural produce based on the red image and the NIR image of the region in the image which is specified by the specification unit and in which the subject that is the agricultural produce is imaged, and in which the growth index computation unit computes a growth index of the agricultural produce based on the growth index image computed by the growth index image computation unit.

(B-7) The information processing system described in (B-6) above, in which the growth index image computation unit computes the growth index image from the reflectance of the near-infrared rays obtained based on the red image and the NIR image of the region in the image which is specified by the specification unit and in which the subject that is the agricultural produce is imaged, and a growth index of the agricultural produce is computed based on the average, the variance, or the high-order variance of the growth index image.

(B-8) The information processing system described in (B-1) above, which further includes an RGB image growth index computation unit that computes an RGB image growth index of the agricultural produce based on the RGB images of the region in the image which is specified by the specification unit and in which the subject that is the agricultural produce is imaged, and in which the growth index computation unit computes a growth index of the agricultural produce based on the RGB image growth index computed by the RGB image growth index computation unit.

(B-9) The information processing system described in (B-8) above, in which the RGB image growth index computation unit computes an RGB image growth index from a ratio of a predetermined color in the RGB image of the region in the image which is specified by the specification unit and in which the subject that is the agricultural produce is imaged.

(B-10) The information processing system described in (B-1) above, which further includes a parallax image growth index computation unit that computes a parallax image growth index based on a parallax image obtained from at least two images obtained by capturing the same subject that is the agricultural produce from different angles, which are RGB images of the region in the image which is specified by the specification unit and in which the subject that is the agricultural produce is imaged, and in which the growth index computation unit computes a growth index of the agricultural produce based on the parallax image growth index computed by the parallax image growth index computation unit.

(B-11) The information processing system described in (B-10) above, in which the parallax image growth index computation unit computes the parallax image growth index from the size of the agricultural produce which is estimated based on the distance to the agricultural produce in an imaging direction, the size being computed based on the parallax image obtained from at least two images obtained by capturing the same subject that is the agricultural produce from different angles, which are RGB images of the region in the image which is specified by the specification unit and in which the subject that is the agricultural produce is imaged.

(B-12) The information processing system described in (B-1) above, which further includes a storage unit that stores a position of the imaging unit, an image captured by the imaging unit, a capturing date and time of the image captured by the imaging unit, and a growth index of each agricultural produce captured by the imaging unit as management information in association with information for identifying the imaging unit, and a harvest time computation unit that computes an anticipated proper harvest time of the agricultural produce based on the growth index of each agricultural produce stored in the storage unit and the relationship of a growth index and a harvest time of each agricultural produce of the past, and in which the storage unit also stores information of the anticipated proper harvest time computed by the harvest time computation unit in association with the information for identifying the imaging unit.

(B-13) The information processing system described in (B-12) above, in which a sensor provided with the imaging unit, a server that manages the storage unit storing the management information, and a terminal device that makes an inquiry of a harvest time to the server are included, and, when an inquiry of the anticipated proper harvest time is received from the terminal device, the server generates response information including the anticipated proper harvest time based on the management information stored in the storage unit in response to the inquiry of the anticipated proper harvest time based on the management information stored in the storage unit, and transmits the response information to the terminal device.

(B-14) An information processing method of an information processing system, which includes: capturing an image of a agricultural produce as an RGB image and a near-infrared ray (NIR) image; specifying a region of the image in which a subject that is the agricultural produce is imaged; and computing a growth index of the agricultural produce based on a growth index image obtained from the RGB image, the NIR image, and a red image of the RGB image of the region in the image which is specified in the specifying and in which the subject is imaged.

(B-15) A program that causes a computer that controls an information processing system to execute: capturing an image of a agricultural produce as an RGB image and a near-infrared ray (NIR) image; specifying a region of the image in which a subject that is the agricultural produce is imaged; and computing a growth index of the agricultural produce based on a growth index image obtained from the RGB image, the NIR image, and a red image of the RGB image of the region in the image which is specified in the specifying and in which the subject is imaged.

(B-16) An imaging device which includes an imaging unit that captures an image of a agricultural produce as an RGB image and a near-infrared ray (NIR) image, a specification unit that specifies a region in the image in which a subject that is the agricultural produce is imaged, and a growth index computation unit that computes a growth index of the agricultural produce based on a growth index image obtained from the RGB image, the NIR image, and a red image of the RGB image of the region in the image which is specified by the specification unit and in which the subject is imaged.

(B-17) The imaging device described in (16) above, in which the growth index image is any one of or a combination of a Normalized Difference Vegetation Index (NDVI) image, a Simple Ratio (SR) image, a Global Environment Monitoring Index (GEMI) image, a Soil Adjusted Vegetation Index (SAVI) image, an Enhanced Vegetation Index (EVI) image, a Perpendicular Vegetation Index (PVI) image, a Photochemical Reflectance Index (PRI) image, a Structure Insensitive Pigment Index (SIPI) image, a Plant Sensing Reflectance Index (PSRI) image, a Chlorophyll Index (CI) image, a Modified Simple Ratio (mSR) image, a Modified Normalized Difference (mND) image, a Canopy Chlorophyll Index (CCI) image, a Water Index (WI) image, a Normalized Difference Water Index (NDWI) image, a Cellulose Absorption Index (CAI) image, a Ratio Vegetation Index (RVI) image, a Kind of Vegetation Index (KVI) image, and a Difference Vegetation Index (DVI) image.

(B-18) The imaging device described in (16) above, in which the imaging unit is configured to include image sensors of each color of the RGB image and an image sensor for a near-infrared ray.

(B-19) An imaging method which includes: capturing an image of a agricultural produce as an RGB image and a near-infrared ray (NIR) image; specifying a region in the image in which a subject that is the agricultural produce is imaged; and computing a growth index of the agricultural produce based on a growth index image obtained from the RGB image, the NIR image, and a red image of the RGB image of the region in the image which is specified in the specifying and in which the subject is imaged.

(B-20) A program that causes a computer that controls an imaging device to execute: capturing an image of a agricultural produce as an RGB image and a near-infrared ray (NIR) image; specifying a region in the image in which a subject that is the agricultural produce is imaged; and computing a growth index of the agricultural produce based on a growth index image obtained from the RGB image, the NIR image, and a red image of the RGB image of the region in the image which is specified in the specifying and in which the subject is imaged.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably. The terms "determine", "calculate" and "compute," and variations thereof, as used herein, are used interchangeably and include any type of methodology, process, mathematical operation or technique.

The term "computer-readable medium" as used herein refers to any tangible storage and/or transmission medium that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the invention is considered to include a tangible storage medium or distribution medium and prior art-recognized equivalents and successor media, in which the software implementations of the present invention are stored.

The term "module" as used herein refers to any known or later developed hardware, software, firmware, artificial intelligence, fuzzy logic, or combination of hardware and software that is capable of performing the functionality associated with that element. Also, while the invention is described in terms of exemplary embodiments, it should be appreciated that individual aspects of the invention can be separately claimed.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 11, 11-1 to 11-N Sensor camera
12, 12-1 to 12-4 Terminal device
13 Network
14 Server
31 Sensor
32 RGB image generation unit
33 NDVI image generation unit
34 Control unit
35 IP address storage unit
36 GPS
37 Environment information measurement unit
38 RTC
39 Growth situation information generation unit
40 Communication unit
41 Communication path specification unit
61 Control unit
62 Inquiring unit
63 Operation unit
64 Communication unit
65 IP address storage unit
66 Display unit
81 Control unit
82 Growth situation information accumulation unit
83 Target region specification unit
84 RGB image growth index computation unit
85 NDVI image growth index computation unit
86 Stereoscopic image growth index computation unit
87 Harvest time computation unit
88 Management information accumulation unit
89 Growth index computation unit
90 Mapping unit
91 Sensor camera operation situation monitoring unit
92 Communication unit
93 Harvest plan creation unit
94 Delivery plan creation unit
95 Sales plan creation unit
96 Purchase plan creation unit
97 Inquiry reception unit
98 Response creation unit

The invention claimed is:

1. Information processing apparatus comprising:
processing circuitry configured to:
acquire image information of an organism comprising a set of image data;
calculate a growth index based on the set of image data;
calculate an anticipated harvest time based on the growth index, wherein the set of image data is obtained from at least two image capture devices, wherein the at least two image capture devices capture the set of image data from at least two different positions; and
calculate a size of the organism based on the set of image data,
wherein the set of image data is obtained using an image sensor comprising a set of RGB color filters provided over a set of infrared (IR) cut filters, wherein the set of IR cut filters is provided over a set of RGB sensors,
wherein the image sensor further comprises a black filter provided over a NIR (near infrared) sensor with no IR cut filter provided over the NIR sensor and therefore with no blocking of NIR from the NIR sensor, and
wherein an image captured from the RGB sensors and the NIR sensor is representative of the organism.

2. The information processing apparatus of claim 1, wherein the image information comprises visible image data and non-visible image data and wherein the visible image data is generated by demosaicing of a RGB pixel signal to provide R, G and B component image signals and wherein the non-visible image data is generated based on a demosaiced R and IR signal.

3. The information processing apparatus of claim 1, wherein the image information comprises visible image data and non-visible image data and wherein the visible image data is generated by demosaicing of a RGB pixel signal to provide R, G and B component image signals and wherein the non-visible image data is generated based on a R and IR signal without demosaicing.

4. The information processing apparatus of claim 1, wherein the image sensor used to obtain the set of image data comprises a stack type image sensor, wherein the stack type image sensor has a blue light sensor layer stacked on a green light sensor layer, wherein the green light sensor layer is stacked on a red light sensor layer, and wherein the red light sensor layer is stacked on a near-infrared ray sensor layer.

5. The information processing apparatus of claim 1, wherein the image sensor used to obtain the set of image data comprises the set of RGB color filters provided over a laminated film, wherein the laminated film comprises at least one of SiO and SiN, and wherein the set of RGB color filters comprises a FR color filter, a FG color filter, and a FB color filter.

6. The information processing apparatus of claim 1, wherein the processing circuitry is configured to calculate parallax image data based on at least two of the image data from the set of image data obtained from the at least two image capture devices and to calculate the growth index based on the parallax image data.

7. Information processing apparatus comprising:
processing circuitry configured to:
acquire image information of an organism comprising a set of image data;
calculate a growth index based on the set of image data; and
calculate an anticipated harvest time based on the growth index,
wherein the set of image data is obtained from at least two image capture devices, wherein the at least two image capture devices capture the set of image data from at least two different positions,
wherein the set of image data is obtained using an image sensor comprising a set of RGB color filters provided over a set of infrared (IR) cut filters, wherein the set of IR cut filters is provided over a set of RGB sensors,
wherein the image sensor further comprises a black filter provided over a NIR (near infrared) sensor with no IR cut filter provided over the NIR sensor and therefore with no blocking of NIR from the NIR sensor, and
wherein an image captured from the RGB sensors and the NIR sensor is representative of the organism.

8. The information processing apparatus of claim 7, wherein the image information comprises visible image data and non-visible image data and wherein the visible image data is generated by demosaicing of a RGB pixel signal to provide R, G and B component image signals and wherein the non-visible image data is generated based on a demosaiced R and IR signal.

9. The information processing apparatus of claim 7, wherein the image information comprises visible image data and non-visible image data and wherein the visible image data is generated by demosaicing of a RGB pixel signal to provide R, G and B component image signals and wherein the non-visible image data is generated based on a Rand IR signal without demosaicing.

10. The information processing apparatus of claim 7, wherein the image sensor used to obtain the set of optical data comprises a stack type image sensor, wherein the stack type image sensor has a blue light sensor layer stacked on a green light sensor layer, wherein the green light sensor layer is stacked on a red light sensor layer, and wherein the red light sensor layer is stacked on a near-infrared ray sensor layer.

11. The information processing apparatus of claim 7, wherein the image sensor used to obtain the set of optical data comprises the set of RGB color filters provided over a laminated film, wherein the laminated film comprises at least one of SiO and SiN, and wherein the set of RGB color filters comprises a FR color filter, a FG color filter, and a FB color filter.

12. The information processing apparatus of claim 7, wherein the processing circuitry is configured to calculate parallax image data based on at least two of the image data from the set of image data obtained from the at least two image capture devices and to calculate the growth index based on the parallax image data.

13. An image sensor comprising:
RGB sensors;
a NIR (near infrared) sensor;
IR (infrared) cut filters over the RGB sensors;
RGB color filters over the IR cut filters; and
a black filter over the NIR sensor with no IR cut filter over the NIR sensor and therefore with no blocking of NIR from the NIR sensor.

14. The image sensor of claim 13, wherein the image sensor used to obtain the set of image data comprises a stack type image sensor, wherein the stack type image sensor has a blue light sensor layer stacked on a green light sensor layer, wherein the green light sensor layer is stacked on a red light sensor layer, and wherein the red light sensor layer is stacked on a near-infrared ray sensor layer.

15. The image sensor of claim 13, wherein the image sensor used to obtain the set of image data comprises the set of RGB color filters provided over a laminated film, wherein the laminated film comprises at least one of SiO and SiN, and wherein the set of RGB color filters comprises a FR color filter, a FG color filter, and a FB color filter.

* * * * *